US011510945B2

(12) United States Patent
Radzioch et al.

(10) Patent No.: US 11,510,945 B2
(45) Date of Patent: Nov. 29, 2022

(54) COMPOSITIONS AND METHODS FOR ENHANCING ION TRANSPORTER ACTIVITY AND USES THEREOF

(71) Applicant: THE ROYAL INSTITUTION FOR THE ADVANCEMENT OF LEARNING/MCGILL UNIVERSITY, Montreal (CA)

(72) Inventors: Danuta Radzioch, Montreal (CA); John Hanrahan, Montreal West (CA); Asmahan Abu-Arish, Verdun (CA); Dusan Garic, Montreal (CA)

(73) Assignee: THE ROYAL INSTITUTION FOR ADVANCEMENT OF LEARNING/MCGILL UNIVERSITY, Montreal (CA)

( * ) Notice: Subject to any disclaimer, the term of this patent is extended or adjusted under 35 U.S.C. 154(b) by 17 days.

(21) Appl. No.: 17/047,678

(22) PCT Filed: Jul. 9, 2018

(86) PCT No.: PCT/CA2018/050832
§ 371 (c)(1),
(2) Date: Oct. 14, 2020

(87) PCT Pub. No.: WO2019/200450
PCT Pub. Date: Oct. 24, 2019

(65) Prior Publication Data
US 2021/0100835 A1    Apr. 8, 2021

Related U.S. Application Data

(60) Provisional application No. 62/658,001, filed on Apr. 16, 2018.

(51) Int. Cl.
| | |
|---|---|
| A61K 33/30 | (2006.01) |
| A61K 9/10 | (2006.01) |
| A61K 31/167 | (2006.01) |
| A61K 31/443 | (2006.01) |
| A61K 31/4439 | (2006.01) |
| A61K 31/47 | (2006.01) |
| A61P 11/00 | (2006.01) |
| A61K 31/404 | (2006.01) |

(52) U.S. Cl.
CPC ............ *A61K 33/30* (2013.01); *A61K 9/10* (2013.01); *A61K 31/167* (2013.01); *A61K 31/404* (2013.01); *A61K 31/443* (2013.01); *A61K 31/4439* (2013.01); *A61K 31/47* (2013.01); *A61P 11/00* (2018.01)

(58) Field of Classification Search
CPC ........ A61K 33/30; A61K 9/10; A61K 31/167; A61K 31/404; A61K 31/443; A61K 31/4439; A61K 31/47; A61P 11/00; C07K 14/705
See application file for complete search history.

(56) References Cited

FOREIGN PATENT DOCUMENTS

WO    2016/011535 A1    1/2016

OTHER PUBLICATIONS

Jessica Johns Pool, Editorial team of CF Foundation compass; CFTR modulators for cystic fibrosis, obtained online on Dec. 5, 2022 (Year: 2022).*
Schmidt et al. (Cystic fibrosis transmembrane conductance regulator modulators in cystic fibrosis: current perspectives), Clinical pharmacology: Advances and Applications; 2016:8 127-140 (Year: 2016).*
Ahmadi et al (Phenotypic profiling of CFTR modulators in patient-derived respiratory epithelia) Genomic medicine; Nature partner Journals, pp. 1-10. (Year: 2017).*
Dusan Garic et al.; Fenretinide differentially modulates the levels of long- and very long-chain ceramides by downregulating Cers5 enzyme: evidence from bench to bedside; J. Mol. Med.; Jul. 10, 2017; vol. 95(10).
Misbahuddin M. Rafeeq et al.; Cystic fibrosis: current therapeutic targets and future approaches, Journal of Translational Medicine; Apr. 27, 2017; vol. 15:84.
S. Van Biervliet et al.; The effect of zinc supplements in cystic fibrosis patients; Ann. Nutr. Metab.; Apr. 29, 2008; vol. 52(2); pp. 152-156.
Anne Bergougnoux et al.; Should diffuse bronchiectasis still be considered a CFTR-related disorder?; Journal of Cystic Fibrosis, Mar. 18, 2015; vol. 14 ; pp. 646-653.
Jennifer L. Taylor-Cousar et al.; Tezacaftor-Ivacaftor in patients with cystic fibrosis homozygous for Phe508del; N. Engl. J. Med.; Nov. 23, 2017; vol. 377; pp. 2013-2023.
Marcus A. Mall et al; Targeting ion channels in cystic fibrosis; Journal of Cystic Fibrosis; Jun. 23, 2015; vol. 14; pp. 561-570.
Andre M. Cantin et al.; Inflammation in cystic fibrosis lung disease: Pathogenesis and therapy; Journal of Cystic fibrosis; Mar. 23, 2015; vol. 14, pp. 419-430.
Massimo Conese et al.; Cystic fibrosis and the innate immune system: Therapeutic implication; Endocrine, Metabolic & Immune disorders—Drug Target; 2011, vol. 11; pp. 8-22.
Marcus A. Mall et al; CFTR: cystic fibrosis and beyond; Eur. Respir. J.; Jun. 12, 2014; vol. 44; pp. 1042-1054.
Valerie Waters et al.; Cystic fibrosis microbiology: Advances in antimicrobial therapy; Journal of Cystic Fibrosis; Feb. 28, 2015; vol. 14; pp. 551-560.

(Continued)

*Primary Examiner* — Mina Haghighatian
(74) *Attorney, Agent, or Firm* — Baker Donelson

(57) ABSTRACT

Methods for enhancing the activity of an ion transporter in a cell and/or treating a channelopathy in a subject based on the administration or use of an effective amount of a fenretinide compound (fenretinide, a fenretinide analog, or a pharmaceutically acceptable salt thereof) and/or zinc are described. The methods are useful for restoring or increasing the cell surface expression of an ion transporter such as the Cystic Fibrosis Transmembrane Conductance Regulator (CFTR) that is mutated or defective. The fenretinide compound and/or zinc may be used in combination with ion transporter modulators, e.g., CFTR modulators, to further enhance the cell surface expression and activity of the ion transporter.

22 Claims, 16 Drawing Sheets

(56) References Cited

OTHER PUBLICATIONS

International Search Report and Written Opinion in respect of PCT/CA2018/050832.

Guilbault et al., Fenretinide Corrects Newly Found Ceramide Deficiency in Cystic Fibrosis. Am J Respir Cell Mol Biol, vol. 38. pp 47-56, 2008.

Guilbault et al., Cystic Fibrosis Fatty Acid Imbalance is Linked to Ceramide Deficiency and Corrected by Fenretinide. Am J Respir Cell Mol Biol vol. 41. pp. 100-106, 2009.

* cited by examiner

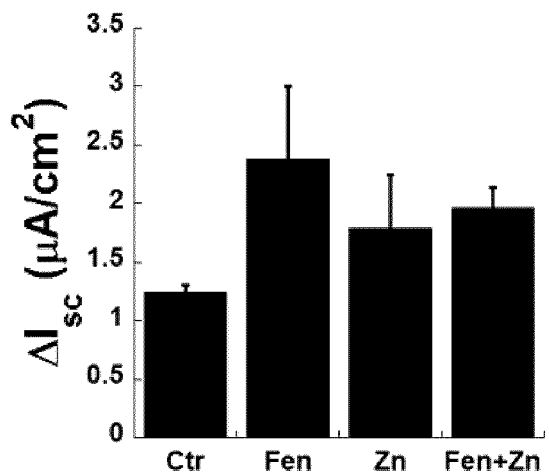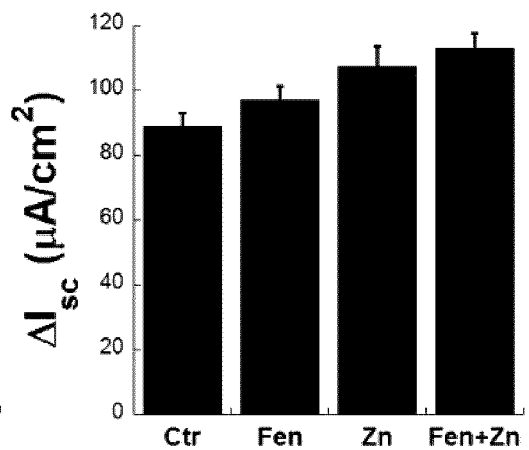
FIG. 4A  FIG. 4B
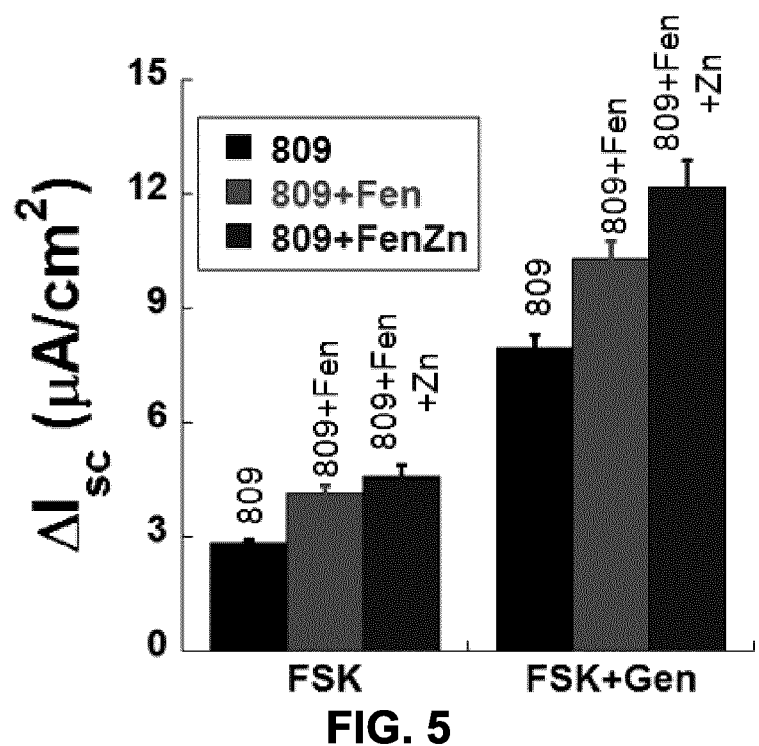
FIG. 5

| Disease | Channel protein | Gene |
|---|---|---|
| Achromatopsia type 2 | Cyclic nucleotide-gated channel, α3 subunit | CNGA3 |
| Achromatopsia type 3 | Cyclic nucleotide-gated channel, β3 subunit | CNGB3 |
| Aland Island eye disease | Cav1.4: calcium channel, voltage-gated, L type, α1F subunit | CACNA1F |
| Andersen-Tawil syndrome | Kir2.1: potassium channel, inwardly-rectifying, subfamily J, member 2 | KCNJ2 |
| Benign familial infantile epilepsy | Nav2.1: sodium channel, voltage-gated, type II, α subunit | SCN2A |
| Benign familial neonatal epilepsy | Kv7.2: potassium channel, voltage-gated, KQT-like subfamily, member 2 | KCNQ2 |
|  | Kv7.3: potassium channel, voltage-gated, KQT-like subfamily, member 3 | KCNQ3 |
| Bestrophinopathy, autosomal-recessive | Bestrophin 1 | BEST1 |
| Central core disease | RyR1: ryanodine receptor 1 | RYR1 |
| Charcot-Marie-Tooth disease type 2C | Transient receptor potential cation channel, subfamily V, member 4 | TRPV4 |
| Childhood absence epilepsy | γ-aminobutyric acid A receptor, α1 subunit | GABRA1 |
|  | γ-aminobutyric acid A receptor, α6 subunit | GABRA6 |
|  | γ-aminobutyric acid A receptor, β3 subunit | GABRB3 |
|  | γ-aminobutyric acid A receptor, γ2 subunit | GABRG2 |
|  | Cav3.2: calcium channel, voltage-gated, T type, α1H subunit | CACNA1H |
| Cognitive impairment with or without cerebellar ataxia | Nav1.6: sodium channel, voltage-gated, type VIII, α subunit | SCN8A |

FIG. 7A

| | | |
|---|---|---|
| Cone-rod dystropy, X-linked, type 3 | Cav1.4: calcium channel, voltage-gated, L type, α1 F subunit | CACNA1F |
| Congenital distal spinal muscular atrophy | Transient receptor potential cation channel, subfamily V, member 4 | TRPV4 |
| Congenital indifference to pain, autosomal-recessive | Nav1.7: Sodium channel, voltage-gated, type IX, α subunit | SCN9A |
| Congenital myasthenic syndrome | Cholinergic receptor, muscle nicotinic, α1 subunit | CHRNA1 |
| | Cholinergic receptor, muscle nicotinic, β1 subunit | CHRNB1 |
| | Cholinergic receptor, muscle nicotinic, δ subunit | CHRND |
| | Cholinergic receptor, muscle nicotinic, ε subunit | CHRNE |
| | Nav1.4: sodium channel, voltage-gated, type IV, α subunit | SCN4A |
| Congenital stationary night blindness type 1C | Transient receptor potential cation channel, subfamily M, member 1 | TRPM1 |
| Congenital stationary night blindness type 2A | Cav1.4: calcium channel, voltage-gated, L type, α1 F subunit | CACNA1F |
| Deafness, autosomal-dominant, type 2A | Kv7.4: potassium channel, voltage-gated, KQT-like subfamily, member 4 | KCNQ4 |
| Deafness, autosomal-recessive, type 4, with enlarged vestibular aqueduct | Kir4.1: potassium channel, inwardly-rectifying, subfamily J, member 10 | KCNJ10 |
| Dravet syndrome | Nav1.1: sodium channel, voltage-gated, type I, α subunit | SCN1A |
| | γ-aminobutyric acid A receptor, γ2 subunit | GABRG2 |
| Early infantile epileptic encephalopathy type 7 | Kv7.2: potassium channel, voltage-gated, KQT-like subfamily, member 2 | KCNQ2 |

FIG. 7B

| | | |
|---|---|---|
| Early infantile epileptic encephalopathy type 11 | Nav2.1: sodium channel, voltage-gated, type II, α subunit | SCN2A |
| Early infantile epileptic encephalopathy type 13 | Nav1.6: sodium channel, voltage-gated, type VIII, α subunit | SCN8A |
| Early infantile epileptic encephalopathy type 14 | KCa4.1: potassium channel, subfamily T, member 1 | KCNT1 |
| EAST/SeSAME syndrome | Kir4.1: potassium channel, inwardly-rectifying, subfamily J, member 10 | KCNJ10 |
| Episodic ataxia type 1 | Kv1.1: potassium channel, voltage-gated, shaker-related subfamily, member 1 | KCNA1 |
| Episodic ataxia type 2 | Cav2.1: calcium channel, voltage-gated, P/Q type, α1 A subunit | CACNA1A |
| Episodic ataxia type 5 | Cavβ4: calcium channel, voltage-gated, β4 subunit | CACNB4 |
| Familial episodic pain syndrome | Transient receptor potential cation channel, subfamily A, member 1 | TRPA1 |
| Familial hemiplegic migraine type 1 | Cav2.1: calcium channel, voltage-gated, P/Q type, α1 A subunit | CACNA1A |
| Familial hemiplegic migraine type 3 | Nav1.1: sodium channel, voltage-gated, type I, α subunit | SCN1A |
| Generalized epilepsy with febrile seizures plus (GEFS+) | Navβ1: sodium channel, voltage-gated, type I, β subunit | SCN1B |
| | Nav1.1: sodium channel, voltage-gated, type I, α subunit | SCN1A |
| | γ-aminobutyric acid A receptor, γ2 subunit | GABRG2 |
| Generalized epilepsy with paroxysmal dyskinesia | KCa1.1: potassium channel, calcium-activated, large conductance, subfamily M, α1 subunit | KCNMA1 |

FIG. 7C

| | | |
|---|---|---|
| Hereditary hyperekplexia | Glycine receptor, α1 subunit | GLRA1 |
| | Glycine receptor, β subunit | GLRB |
| Hyperkalemic periodic paralysis | Nav1.4: sodium channel, voltage-gated, type IV, α subunit | SCN4A |
| Hypokalemic periodic paralysis type 1 | Cav1.1: calcium channel, voltage-gated, L type, α1S subunit | CACNA1S |
| Hypokalemic periodic paralysis type 2 | Nav1.4: sodium channel, voltage-gated, type IV, α subunit | SCN4A |
| Juvenile macular degeneration | Cyclic nucleotide-gated channel, β3 subunit | CNGB3 |
| Juvenile myoclonic epilepsy | γ-aminobutyric acid A receptor, α1 subunit | GABRA1 |
| | Cavβ4: calcium channel, voltage-gated, β4 subunit | CACNB4 |
| Malignant hyperthermia susceptibility | RyR1: ryanodine receptor 1 | RYR1 |
| | Cav1.1: calcium channel, voltage-gated, L type, α1S subunit | CACNA1S |
| Mucolipidosis type IV | TRPML1/mucolipin 1 | MCOLN1 |
| Multiple pterygium syndrome, lethal type | Cholinergic receptor, muscle nicotinic, α1 subunit | CHRNA1 |
| | Cholinergic receptor, muscle nicotinic, δ subunit | CHRND |
| | Cholinergic receptor, muscle nicotinic, γ subunit | CHRNG |
| Multiple pterygium syndrome, nonlethal type (Escobar variant) | Cholinergic receptor, muscle nicotinic, γ subunit | CHRNG |
| Myotonia congenita, autosomal-dominant (Thomsen disease) | ClC-1: chloride channel 1, voltage-gated | CLCN1 |
| Myotonia congenita, autosomal-recessive (Becker disease) | ClC-1: chloride channel 1, voltage-gated | CLCN1 |
| Nocturnal frontal lobe epilepsy type 1 | Cholinergic receptor, neuronal nicotinic, α4 subunit | CHRNA4 |
| Nocturnal frontal lobe epilepsy type 3 | Cholinergic receptor, neuronal nicotinic, β2 subunit | CHRNB2 |

FIG. 7D

| Disease | Channel | Gene |
|---|---|---|
| Nocturnal frontal lobe epilepsy type 4 | Cholinergic receptor, neuronal nicotinic, α2 subunit | CHRNA2 |
| Nocturnal frontal lobe epilepsy type 5 | KCa4.1: potassium channel, subfamily T, member 1 | KCNT1 |
| Paramyotonia congenita | Nav1.4: sodium channel, voltage-gated, type IV, α subunit | SCN4A |
| Paroxysmal extreme pain disorder | Nav1.7: Sodium channel, voltage-gated, type IX, α subunit | SCN9A |
| Potassium-aggravated myotonia | Nav1.4: sodium channel, voltage-gated, type IV, α subunit | SCN4A |
| Primary erythermalgia | Nav1.7: sodium channel, voltage-gated, type IX, α subunit | SCN9A |
| Retinitis pigmentosa type 45, autosomal-recessive | Cyclic nucleotide-gated channel, β1 subunit | CNGB1 |
| Retinitis pigmentosa type 49, autosomal-recessive | Cyclic nucleotide-gated channel, α1 subunit | CNGA1 |
| Retinitis pigmentosa type 50, autosomal-dominant | Bestrophin 1 | BEST1 |
| Scapuloperoneal spinal muscular atrophy | Transient receptor potential cation channel, subfamily V, member 4 | TRPV4 |
| Small fiber neuropathy | Nav1.7: sodium channel, voltage-gated, type IX, α subunit | SCN9A |
| Spinocerebellar ataxia type 6 | Cav2.1: calcium channel, voltage-gated, P/Q type, α1A subunit | CACNA1A |
| Spinocerebellar ataxia type 13 | Kv3.3: potassium channel, voltage-gated, Shaw-related subfamily, member 3 | KCNC3 |
| Vitelliform macular dystrophy | Bestrophin 1 | BEST1 |
| Vitreoretinochoroidopathy | Bestrophin 1 | BEST1 |

FIG. 7E

| Disease | Channel protein | Gene |
|---|---|---|
| Atrial standstill | Nav1.5: sodium channel, voltage-gated, type V, α subunit | SCN5A |
| Brugada syndrome type 1 | Nav1.5: sodium channel, voltage-gated, type V, α subunit | SCN5A |
| Brugada syndrome type 3 (short QT syndrome type 4) | Cav1.2: calcium channel, voltage-gated, L type, α1C subunit | CACNA1C |
| Brugada syndrome type 4 (short QT syndrome type 5) | Cavβ2: calcium channel, voltage-gated, β2 subunit | CACNB2 |
| Brugada syndrome type 5 | Navβ1: sodium channel, voltage-gated, type I, β subunit | SCN1B |
| Brugada syndrome type 6 | Potassium channel, voltage-gated, Isk-related subfamily, member 3 | KCNE3 |
| Brugada syndrome type 7 | Navβ3: sodium channel, voltage-gated, type III, β subunit | SCN3B |
| Brugada syndrome type 8 | Hyperpolarization-activated cyclic nucleotide-gated potassium channel 4 | HCN4 |
| Catecholaminergic polymorphic ventricular tachycardia type 2 | RyR2: ryanodine receptor 2 | RYR2 |
| Dilated cardiomyopathy type 1E | Nav1.5: sodium channel, voltage-gated, type V, α subunit | SCN5A |
| Dilated cardiomyopathy type 10 | ATP-binding cassette, subfamily C, member 9 (sulfonylurea receptor 2) | ABCC9 |
| Familial arrhythmogenic right ventricular dysplasia type 2 | RyR2: ryanodine receptor 2 | RYR2 |
| Familial atrial fibrillation type 3 | Kv7.1: potassium channel, voltage-gated, KQT-like subfamily, member 1 | KCNQ1 |
| Familial atrial fibrillation type 4 | Potassium channel, voltage-gated, Isk-related subfamily, member 2 | KCNE2 |

FIG. 8A

| | | |
|---|---|---|
| Familial atrial fibrillation type 7 | Kv1.5: potassium channel, voltage-gated, shaker-related subfamily, member 5 | KCNA5 |
| Familial atrial fibrillation type 9 | Kir2.1: potassium channel, inwardly-rectifying, subfamily J, member 2 | KCNJ2 |
| Familial atrial fibrillation type 10 | Nav1.5: sodium channel, voltage-gated, type V, α subunit | SCN5A |
| Familial atrial fibrillation type 12 | ATP-binding cassette, subfamily C, member 9 | ABCC9 |
| Jervell and Lange-Nielsen syndrome type 1 | Kv7.1: potassium channel, voltage-gated, KQT-like subfamily, member 1 | KCNQ1 |
| Jervell and Lange-Nielsen syndrome type 2 | Potassium channel, voltage-gated, Isk-related subfamily, member 1 | KCNE1 |
| Long QT syndrome type 1 | Kv7.1: potassium channel, voltage-gated, KQT-like subfamily, member 1 | KCNQ1 |
| Long QT syndrome type 2 | Kv11.1: potassium channel, voltage-gated, subfamily H, member 2 | KCNH2 |
| Long QT syndrome type 3 | Nav1.5: sodium channel, voltage-gated, type V, α subunit | SCN5A |
| Long QT syndrome type 5 | Potassium channel, voltage-gated, Isk-related subfamily, member 1 | KCNE1 |
| Long QT syndrome type 6 | Potassium channel, voltage-gated, Isk-related subfamily, member 2 | KCNE2 |
| Long QT syndrome type 7 (Andersen-Tawil syndrome) | Kir2.1: potassium channel, inwardly-rectifying, subfamily J, member 2 | KCNJ2 |
| Long QT syndrome type 8 (Timothy syndrome) | Cav1.2: calcium channel, voltage-gated, L type, α1C subunit | CACNA1C |
| Long QT syndrome type 10 | Navβ4: sodium channel, voltage-gated, type IV, β subunit | SCN4B |

FIG. 8B

| Disease | Protein | Gene |
|---|---|---|
| Long QT syndrome type 13 | Kir3.4: potassium channel, inwardly-rectifying, subfamily J, member 5 | KCNJ5 |
| Nonprogressive familial heart block | Nav1.5: sodium channel, voltage-gated, type V, α subunit | SCN5A |
| Paroxysmal familial ventricular fibrillation, type 1 | Nav1.5: sodium channel, voltage-gated, type V, α subunit | SCN5A |
| Progressive familial heart block type IA (Lenegre-Lev syndrome) | Nav1.5: sodium channel, voltage-gated, type V, α subunit | SCN5A |
| Progressive familial heart block type IB | Transient receptor potential cation channel, subfamily M, member 4 | TRPM4 |
| Short QT syndrome type 1 | Kv11.1: potassium channel, voltage-gated, subfamily H, member 2 | KCNH2 |
| Short QT syndrome type 2 | Kv7.1: potassium channel, voltage-gated, KQT-like subfamily, member 1 | KCNQ1 |
| Short QT syndrome type 3 | Kir2.1: potassium channel, inwardly-rectifying, subfamily J, member 2 | KCNJ2 |
| Short QT syndrome type 4 (Brugada syndrome type 3) | Cav1.2: calcium channel, voltage-gated, L type, α1C subunit | CACNA1C |
| Short QT syndrome type 5 (Brugada syndrome type 4) | Cavβ2: calcium channel, voltage-gated, β2 subunit | CACNB2 |
| Short QT syndrome type 6 | Cavα2δ1: calcium channel, voltage-gated, α2/δ1 subunit | CACNA2D |
| Sick sinus syndrome type 1, autosomal-recessive | Nav1.5: sodium channel, voltage-gated, type V, α subunit | SCN5A |
| Sick sinus syndrome type 2, autosomal-dominant | Hyperpolarization-activated cyclic nucleotide-gated potassium channel 4 | HCN4 |

FIG. 8C

| Disease | Channel protein | Gene |
|---|---|---|
| Permanent neonatal diabetes mellitus | SUR1: ATP-binding cassette, subfamily C, member 8 | ABCC8 |
| | Kir6.2: potassium channel, inwardly-rectifying, subfamily J, member 11 | KCNJ11 |
| Transient neonatal diabetes mellitus type 2 | SUR1: ATP-binding cassette, subfamily C, member 8 | ABC8B |
| Transient neonatal diabetes mellitus type 3 | Kir6.2: potassium channel, inwardly-rectifying, subfamily J, member 11 | KCNJ11 |
| Familial hyperinsulinemic hypoglycemia type 1 | SUR1: ATP-binding cassette, subfamily C, member 8 | ABCC8 |
| Familial hyperinsulinemic hypoglycemia type 2 | Kir6.2: potassium channel, inwardly-rectifying, subfamily J, member 11 | KCNJ11 |
| Leucine-induced hypoglycemia of infancy | SUR1: ATP-binding cassette, subfamily C, member 8 | ABCC8 |
| Thyrotoxic periodic paralysis | Kir2.6: potassium channel, inwardly-rectifying, subfamily J, member 18 | KCNJ18 |
| Familial hyperaldosteronism type 3 | Kir3.4: potassium channel, inwardly-rectifying, subfamily J, member 5 | KCNJ5 |
| Osteopetrosis, autosomal dominant, type 2 | ClC-7: chloride channel 7, voltage-gated | CLCN7 |
| Osteopetrosis, autosomal recessive, type 4 | ClC-7: chloride channel 7, voltage-gated | CLCN7 |
| Osteopetrosis, autosomal recessive, type 5 | Osteopetrosis-associated transmembrane protein 1 | OSTM1 |

FIG. 9

| Disease | Channel protein | Gene |
|---|---|---|
| Nephrogenic diabetes insipidus, autosomal | Aquaporin 2 | AQP2 |
| Pseudohypoaldosteronism type 1, autosomal-recessive | Sodium channel, nonvoltage-gated 1, α subunit | SCNN1A |
| Liddle syndrome | Sodium channel, nonvoltage-gated 1, β subunit | SCNN1B |
| | Sodium channel, nonvoltage-gated 1, γ subunit | SCNN1G |
| | Sodium channel, nonvoltage-gated 1, β subunit | SCNN1B |
| | Sodium channel, nonvoltage-gated 1, γ subunit | SCNN1G |
| Bartter syndrome type 2 | Kir1.1: potassium channel, inwardly-rectifying, subfamily J, member 1 | KCNJ1 |
| Bartter syndrome type 3 | ClC-Kb: chloride channel, kidney, B | CLCNKB |
| Bartter syndrome type 4A | Barttin | BSND |
| Bartter syndrome type 4B | ClC-Ka: chloride channel, kidney, A & ClC-Kb: chloride channel, kidney, B | CLCNKA & CLCNKB |
| Hypomagnesemia with secondary hypocalcemia | Transient receptor potential cation channel, subfamily M, member 6 | TRPM6 |
| Focal segmental glomerulosclerosis type 2 | Transient receptor potential cation channel, subfamily C, member 6 | TRPC6 |
| Polycystic kidney disease type 2 | Polycystin 2 | PKD2 |

FIG. 10

COMPOSITIONS AND METHODS FOR ENHANCING ION TRANSPORTER ACTIVITY AND USES THEREOF

CROSS REFERENCE TO RELATED APPLICATIONS

This application claims priority of U.S. provisional application Ser. No. 62/658,001, filed on Apr. 16, 2018, which is incorporated herein by reference in its entirety.

TECHNICAL FIELD

The present invention generally relates to the enhancement of ion transporter activity, and more particularly to the treatment of diseases associated with defective ion transporter function.

BACKGROUND ART

Ion transporters or ion channels provide pores for the passive diffusion of ions across biological membranes. They are often highly selective for a particular ionic species, leading to a classification into sodium ($Na^+$), potassium ($K^+$), calcium ($Ca^{2+}$), chloride ($Cl^-$) and unspecific cation channels. The direction of net ion transport, which is associated with an electric current, depends on the electrochemical gradient for the relevant ionic species. These gradients are established by an interplay of active pumps, co-transporters and ion channels. Ion channels can close and open in a process called gating. This allows many types of regulation. Thus, there are ligand-gated channels (e.g. postsynaptic GABA- or glutamate-receptor channels), voltage-gated, swelling- or stretch-activated, and heat- or cold-activated channels. In addition, channels may be regulated for example by calcium, pH, phosphorylation and lipids.

While the role of ion channels in generating electric currents (the basis of neuronal signalling) is probably known best, channels have many other functions. For instance, ion channels are involved in the trans-epithelial transport of salt and water, for the regulation of cellular volume and pH, for the acidification of intracellular organelles, and (in particular in the case of $Ca^{2+}$ channels), for chemical signalling. Hence, although many ion channel diseases (sometimes referred to as channelopathies) affect the neuromuscular system and cause diseases such as epilepsy, ataxia, myotonia and cardiac arrhythmia, they may affect many other organs. Defects in trans-epithelial transport underlie, for example, cystic fibrosis (CF) and several forms of Bartter syndrome, mutations in ATP-sensitive $K^+$ channels severely affect insulin secretion, and mutations in endosomal and lysosomal $Cl^-$ channels can cause kidney stones and osteopetrosis, respectively.

The Cystic Fibrosis Transmembrane Conductance Regulator (CFTR) is an ion channel that mediates cAMP-stimulated chloride and bicarbonate secretion in the airways. Loss-of-function mutations in the cftr gene cause CF, however an acquired deficiency in CFTR also occurs in other diseases of mucus clearance including COPD with chronic bronchitis (Raju et al 2016), asthma, as well as in idiopathic pancreatitis, respiratory conditions such as rhinosinusitis and bronchiectasis, and congenital bilateral absence of the vas deferens.

CFTR modulators such as the channel potentiators ivacaftor (IVA, VX-770), GLPG2451 and GLPG1837, which increase the probability of channel opening, and correctors lumacaftor (LUM, VX-809), tezacaftor (VX-661), and GLPG2222, all offer hope for individuals with CF who are homozygous for F508del and also for those with a second non-gating mutation. CFTR modulators are expected to improve CFTR function and reduce the progression of CF lung disease, the main cause of morbidity and mortality among CF patients (Rowe et al., 2017). However, preliminary results from clinical trials with these compounds suggest that CFTR modulators to date are ineffective for a significant fraction of homozygous CFTR F508del patients, who do not respond to CFTR therapies and have FEV1% (ratio of forced expiratory volume 1 second and forced vital capacity of lungs) that continue to decline after each exacerbation.

Thus, there is a need for the development of novel approaches for the treatment of channelopathies, including diseases associated with CFTR mutations such as CF.

The present description refers to a number of documents, the content of which is herein incorporated by reference in their entirety.

SUMMARY OF THE INVENTION

In aspects, the present disclosure provides the following items 1 to 78:

1. A method for enhancing the activity of an ion transporter in a cell, the method comprising contacting the cell with an effective amount of (i) fenretinide, a fenretinide analog, or a salt thereof; (ii) zinc; or (iii) a combination of (i) and (ii).
2. The method of item 1, wherein the ion transporter is a mutated or defective ion transporter have reduced cell surface expression and/or activity relative to the corresponding native ion transporter.
3. The method of item 1 or 2, wherein the ion transporter is not Cystic Fibrosis Transmembrane Conductance Regulator (CFTR).
4. The method of item 1 or 2, wherein the ion transporter is Cystic Fibrosis Transmembrane Conductance Regulator (CFTR), and wherein the method comprises contacting the cell with an effective amount of a combination of (i) fenretinide, a fenretinide analog, or a salt thereof; and (ii) zinc.
5. The method of item 4, wherein the CFTR is a mutated CFTR.
6. The method of item 5, wherein the mutated CFTR comprises a mutation at position 508 of the CFTR protein.
7. The method of item 6, wherein the mutation at position 508 of the CFTR protein is a deletion.
8. A method for treating a channelopathy in a subject, the method comprising administering to said subject an effective amount of (i) fenretinide, a fenretinide analog, or a pharmaceutically acceptable salt thereof; (ii) a physiologically acceptable source of assimilable zinc; or (iii) a combination of (i) and (ii).
9. The method of item 8, wherein the channelopathy is caused by a mutated or defective ion transporter having reduced cell surface expression and/or activity relative to the corresponding native ion transporter.
10. The method of item 9, wherein the ion transporter is not Cystic Fibrosis Transmembrane Conductance Regulator (CFTR).
11. The method of item 9, wherein the ion transporter is Cystic Fibrosis Transmembrane Conductance Regulator (CFTR).
12. The method of item 11, wherein the channelopathy is cystic fibrosis (CF), chronic obstructive pulmonary disease (COPD), asthma, idiopathic pancreatitis, rhinosinusitis, bronchiectasis, or congenital bilateral absence of the vas deferens.

13. The method of item 12, wherein the channelopathy is COPD, asthma, idiopathic pancreatitis, rhinosinusitis, bronchiectasis, or congenital bilateral absence of the vas deferens.
14. The method of any one of items 8 to 13, wherein the channelopathy is a respiratory system channelopathy.
15. The method of item 12 or 14, wherein the channelopathy is CF.
16. The method of any one of items 12 to 14, wherein the CFTR is a mutated CFTR.
17. The method of item 16, wherein the mutated CFTR comprises a mutation of the phenylalanine residue at position 508 of the CFTR protein.
18. The method of item 17, wherein the mutation at position 508 of the CFTR protein is a deletion (ΔF508).
19. The method of any one of items 9 to 18, wherein the mutation is a homozygous mutation.
20. The method of any one of items 8 to 19, wherein said subject suffers from zinc deficiency.
21. The method of any one of items 8 to 20, wherein said method comprises administering an effective amount of a combination of (i) fenretinide, a fenretinide analog, or a pharmaceutically acceptable salt thereof; and (ii) a physiologically acceptable source of assimilable zinc.
22. The method of any one of items 8 to 21, wherein said method comprises administering an effective amount of fenretinide.
23. The method of any one of items 8 to 22, wherein said physiologically acceptable source of assimilable zinc is zinc oxide or a pharmaceutically acceptable zinc salt.
24. The method of item 23, wherein said pharmaceutically acceptable zinc salt is zinc sulfate.
25. The method of any one of items 8 to 24, wherein the effective amount of fenretinide, fenretinide analog or salt thereof that is administered provides a plasma concentration of the fenretinide, fenretinide analog or salt thereof of about 0.5 µM to about 6 µM, preferably of about 1 µM to about 2.5 or 3 µM, in said subject.
26. The method of any one of items 8 to 25, wherein the effective amount of fenretinide, fenretinide analog or salt thereof that is administered is about 1 mg to about 500 mg, preferably about 10 mg to 250 mg.
27. The method of any one of items 8 to 26, wherein the effective amount of physiologically acceptable source of assimilable zinc that is administered provides a plasma concentration of zinc of about 10 µM to about 15 µM in the subject.
28. The method of any one of items 8 to 27, wherein the effective amount of physiologically acceptable source of assimilable zinc that is administered comprises about 1 mg to about 200 mg of elemental zinc, preferably about 5 mg to about 50 mg of elemental zinc.
29. The method of any one of items 8 to 28, wherein the (i) fenretinide, fenretinide analog or salt thereof is present in amorphous form in a solid dispersion comprising a matrix polymer.
30. The method of item 29, wherein the matrix polymer is a polyvinylpyrrolidone polymer, preferably a polyvinylpyrrolidone polymer sold under the trade-name Plasdone® (povidones), polyvinylpyrrolidone K12, polyvinylpyrrolidone K17, polyvinylpyrrolidone K25, polyvinylpyrrolidone K30, polyvinylpyrrolidone K90, or any combination thereof.
31. The method of any one of items 8 to 30, wherein the (i) fenretinide, fenretinide analog or salt thereof; and (ii) physiologically acceptable source of assimilable zinc, are formulated in the same composition.
32. The method of any one of items 8 to 31, wherein the method further comprises administering an effective amount of an ion transporter modulator.
33. The method of item 32, wherein the ion transporter modulator is a CFTR modulator.
34. The method of item 33, wherein the CFTR modulator is ivacaftor (IVA, VX-770), GLPG2451, GLPG1837, lumacaftor (LUM, VX-809), tezacaftor (VX-661), VX-440, VX-152, GLPG2222, or any combination thereof.
35. The method of item 34, wherein the CFTR modulator comprise a combination of ivacaftor and lumacaftor or tezacaftor and ivacaftor.
36. The method of item 35, wherein the combination further comprises VX-440 or VX-152.
37. Use of (i) fenretinide, a fenretinide analog, or a salt thereof; (ii) zinc; or (iii) a combination of (i) and (ii) for enhancing the activity of an ion transporter in a cell.
38. Use of (i) fenretinide, a fenretinide analog, or a salt thereof; (ii) zinc; or (iii) a combination of (i) and (ii) for the manufacture of a medicament for enhancing the activity of an ion transporter in a cell.
39. An agent for use in enhancing the activity of an ion transporter in a cell, wherein the agent is (i) fenretinide, a fenretinide analog, or a salt thereof; (ii) zinc; or (iii) a combination of (i) and (ii).
40. A combination for use in enhancing the activity of an ion transporter in a cell, wherein the combination comprises (i) fenretinide, a fenretinide analog, or a salt thereof and (ii) zinc.
41. The use, agent for use, or combination for use of any one of items 37 to 40, wherein the ion transporter is a mutated or defective ion transporter have reduced cell surface expression and/or activity relative to the corresponding native ion transporter.
42. The use, agent for use, or combination for use of any one of items 37 to 41, wherein the ion transporter is not Cystic Fibrosis Transmembrane Conductance Regulator (CFTR).
43. The use, agent for use, or combination for use of any one of items 37 to 41, wherein the ion transporter is Cystic Fibrosis Transmembrane Conductance Regulator (CFTR), and wherein the method comprises contacting the cell with an effective amount of a combination of (i) fenretinide, a fenretinide analog, or a salt thereof; and (ii) zinc.
44. The use, agent for use, or combination for use of item 43, wherein the CFTR is a mutated CFTR.
45. The use, agent for use, or combination for use of item 44, wherein the mutated CFTR comprises a mutation at position 508 of the CFTR protein.
46. The use, agent for use, or combination for use of item 45, wherein the mutation at position 508 of the CFTR protein is a deletion.
47. Use of (i) fenretinide, a fenretinide analog, or a pharmaceutically acceptable salt thereof; (ii) a physiologically acceptable source of assimilable zinc; or (iii) a combination of (i) and (ii) for treating a channelopathy in a subject.
48. Use of (i) fenretinide, a fenretinide analog, or a pharmaceutically acceptable salt thereof; (ii) a physiologically acceptable source of assimilable zinc; or (iii) a combination of (i) and (ii) for the manufacture of a medicament for treating a channelopathy in a subject.

49. An agent for use in treating a channelopathy in a subject, wherein the wherein the agent is (i) fenretinide, a fenretinide analog, or a pharmaceutically acceptable salt thereof; (ii) a physiologically acceptable source of assimilable zinc; or (iii) a combination of (i) and (ii).

50. A combination for use in treating a channelopathy in a subject, wherein the combination comprises (i) fenretinide, a fenretinide analog, or a pharmaceutically acceptable salt thereof; and (ii) a physiologically acceptable source of assimilable zinc.

51. The use, agent for use, or combination for use of any one of items 47 to 50, wherein the channelopathy is caused by a mutated or defective ion transporter having reduced cell surface expression and/or activity relative to the corresponding native ion transporter.

52. The use, agent for use, or combination for use of item 51, wherein the ion transporter is not Cystic Fibrosis Transmembrane Conductance Regulator (CFTR).

53. The use, agent for use, or combination for use of item 51, wherein the ion transporter is Cystic Fibrosis Transmembrane Conductance Regulator (CFTR).

54. The use, agent for use, or combination for use of item 53, wherein the channelopathy is cystic fibrosis (CF), chronic obstructive pulmonary disease (COPD), asthma, idiopathic pancreatitis, rhinosinusitis, bronchiectasis, or congenital bilateral absence of the vas deferens.

55. The use, agent for use, or combination for use of item 54, wherein the channelopathy is COPD, asthma, idiopathic pancreatitis, rhinosinusitis, bronchiectasis, or congenital bilateral absence of the vas deferens.

56. The use, agent for use, or combination for use of any one of items 47 to 55, wherein the channelopathy is a respiratory system channelopathy.

57. The use, agent for use, or combination for use of item 54 or 56, wherein the channelopathy is CF.

58. The use, agent for use, or combination for use of any one of items 54 to 56, wherein the CFTR is a mutated CFTR.

59. The use, agent for use, or combination for use of item 58, wherein the mutated CFTR comprises a mutation of the phenylalanine residue at position 508 of the CFTR protein.

60. The use, agent for use, or combination for use of item 59, wherein the mutation at position 508 of the CFTR protein is a deletion ($\Delta$F508).

61. The use, agent for use, or combination for use of any one of items 51 to 60, wherein the mutation is a homozygous mutation.

62. The use, agent for use, or combination for use of any one of items 47 to 61, wherein said subject suffers from zinc deficiency.

63. The use, agent for use, or combination for use of any one of items 47 to 62, wherein a combination of (i) fenretinide, a fenretinide analog, or a pharmaceutically acceptable salt thereof; and (ii) a physiologically acceptable source of assimilable zinc is used.

64. The use, agent for use, or combination for use of any one of items 47 to 63, wherein fenretinide is used.

65. The use, agent for use, or combination for use of any one of items 47 to 64, wherein said physiologically acceptable source of assimilable zinc is zinc oxide or a pharmaceutically acceptable zinc salt.

66. The use, agent for use, or combination for use of item 65, wherein said pharmaceutically acceptable zinc salt is zinc sulfate.

67. The use, agent for use, or combination for use of any one of items 47 to 66, wherein the amount of fenretinide, fenretinide analog or salt thereof that is used provides a plasma concentration of the fenretinide, fenretinide analog or salt thereof of about 0.5 µM to about 6 µM, preferably of about 1 µM to about 2.5 or 3 µM, in said subject.

68. The use, agent for use, or combination for use of any one of items 47 to 67, wherein the amount of fenretinide, fenretinide analog or salt thereof that is used is about 1 mg to about 500 mg, preferably about 10 mg to 250 mg.

69. The use, agent for use, or combination for use of any one of items 47 to 68, wherein the amount of physiologically acceptable source of assimilable zinc that is used provides a plasma concentration of zinc of about 10 µM to about 15 µM in the subject.

70. The use, agent for use, or combination for use of any one of items 47 to 69, wherein the amount of physiologically acceptable source of assimilable zinc that is used comprises about 1 mg to about 200 mg of elemental zinc, preferably about 5 mg to about 50 mg of elemental zinc.

71. The use, agent for use, or combination for use of any one of items 47 to 70, wherein the (i) fenretinide, fenretinide analog or salt thereof is present in amorphous form in a solid dispersion comprising a matrix polymer.

72. The use, agent for use, or combination for use of item 71, wherein the matrix polymer is a polyvinylpyrrolidone polymer, preferably a polyvinylpyrrolidone polymer sold under the trade-name Plasdone® (povidones), polyvinylpyrrolidone K12, polyvinylpyrrolidone K17, polyvinylpyrrolidone K25, polyvinylpyrrolidone K30, polyvinylpyrrolidone K90, or any combination thereof.

73. The use, agent for use, or combination for use of any one of items 47 to 72, wherein the (i) fenretinide, fenretinide analog or salt thereof; and (ii) physiologically acceptable source of assimilable zinc, are formulated in the same composition.

74. The use, agent for use, or combination for use of any one of items 47 to 73, which further comprises the use of an ion transporter modulator.

75. The use, agent for use, or combination for use of item 74, wherein the ion transporter modulator is a CFTR modulator.

76. The use, agent for use, or combination for use of item 75, wherein the CFTR modulator is ivacaftor (IVA, VX-770), GLPG2451, GLPG1837, lumacaftor (LUM, VX-809), tezacaftor (VX-661), VX-440, VX-152, GLPG2222, or any combination thereof.

77. The use, agent for use, or combination for use of item 76, wherein the CFTR modulator comprise a combination of ivacaftor and lumacaftor or tezacaftor and ivacaftor.

78. The use, agent for use, or combination for use of item 77, wherein the combination further comprises VX-440 or VX-152.

Other objects, advantages and features of the present invention will become more apparent upon reading of the following non-restrictive description of specific embodiments thereof, given by way of example only with reference to the accompanying drawings.

BRIEF DESCRIPTION OF DRAWINGS

In the appended drawings:

FIGS. 4A-B are graphs showing the effect of Zinc and/or Fenretinide treatment on CFTR-mediated secretion. Ussing Chambers were used to measure F508del-CFTR (FIG. 4A) and wt-CFTR (FIG. 4B) functional expression as short-circuit current across polarized bronchial epithelial cells in response to forskolin (FSK). Treatment: Cells were treated basally or not with 1.25 µM Fenretinide (Fen), 12.5 µM Zinc (Zn) or a combination of 1.25 µM Fenretinide and 12.5 µM Zinc (Fen+Zn) for 3 days with VX-809 bilaterally for the last 24. Unpaired Student t-test was used for statistical analysis.

FIG. 5 is a graph showing the effect of Zinc and/or Fenretinide treatment on F508del-CFTR function after partial rescue by VX-809 (809) in the absence and presence of 50 µM of the potentiator genistein (acts similarly to VX770). Ussing Chambers were used to measure F508del-CFTR conductance by measuring the short-circuit current across basally permeabilized polarized cells in response to forskolin (FSK) or forskolin+genistein (FSK+Gen). Treatment: Cells were treated basally or not with 1.25 µM fenretinide (Fen) or the combination a combination of 1.25 µM Fenretinide and 12.5 µM Zinc (FenZn) for 3 days. 1 µM VX-809 was added bilaterally during the last 24h. Unpaired student t-test was used for statistical analysis.

FIGS. 7A-7E show a list of representative channelopathies affecting the nervous system, and the associated defective genes/proteins (from June-Bum Kim, *Korean J Pediatr.* 2014 January; 57(1): 1-18).

FIGS. 8A-8C show a list of representative channelopathies affecting the cardiovascular system, and the associated dysfunctional genes/proteins (from June-Bum Kim, *Korean J Pediatr.* 2014 January; 57(1): 1-18).

FIG. 9 shows a list of representative channelopathies affecting the endocrine system, and the associated dysfunctional genes/proteins (from June-Bum Kim, *Korean J Pediatr.* 2014 January; 57(1): 1-18).

FIG. 10 shows a list of representative channelopathies affecting the urinary system (i.e., renal channelopathies), and the associated dysfunctional genes/proteins (from June-Bum Kim, *Korean J Pediatr.* 2014 January; 57(1): 1-18).

DISCLOSURE OF INVENTION

Figure 1:
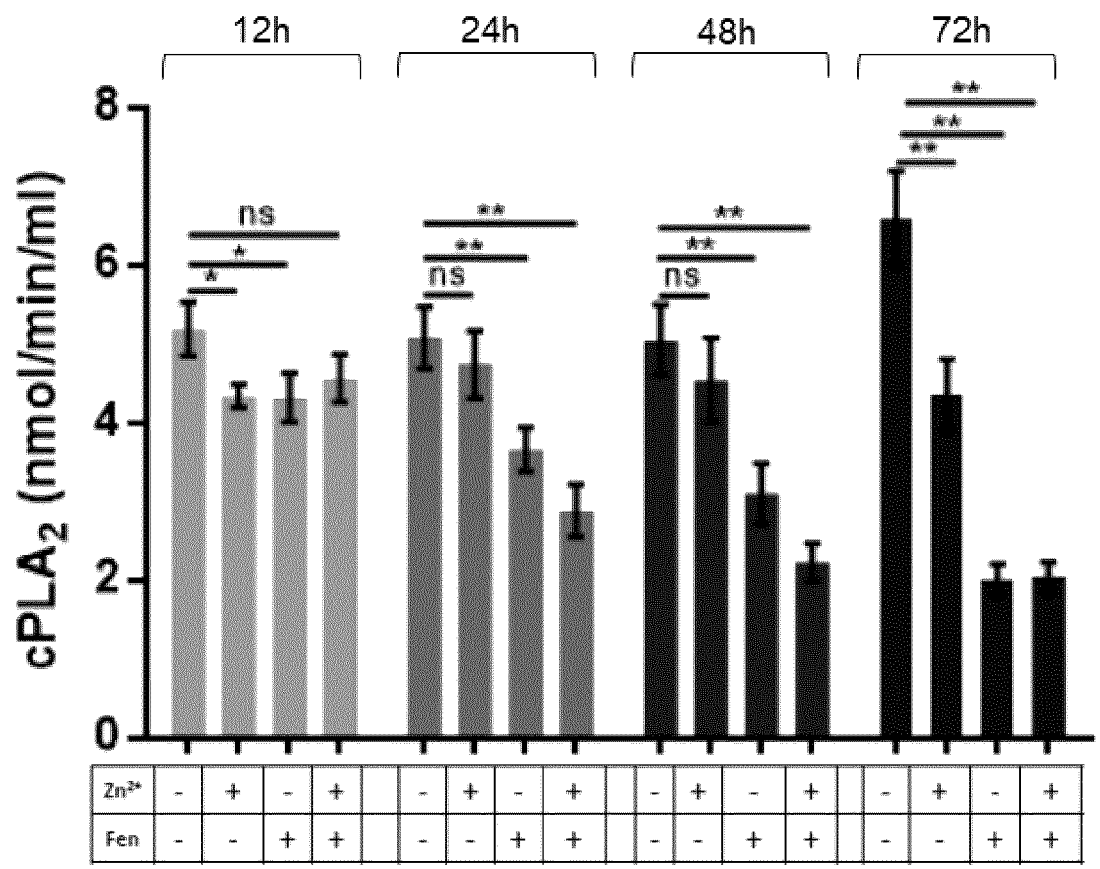
FIG. 1 is a graph showing the effect of fenretinide and $Zn^{2+}$ treatment on the activity of cytoplasmic phospholipases ($cPLA_2$). Lung epithelial cells were treated with 1.25 µM fenretinide (Fen) and/or 12.5 µM zinc sulfate ($Zn^{2+}$) for 12, 24, 48 or 72 hours and the activity of $PLA_2$ was assessed using a commercially available ELISA kit (Abcam, cat. No. ab133090). All statistical analyses were performed using GraphPad™ software (GraphPad, San Diego, Calif., USA). Statistical significance of differences was evaluated using unpaired t-test with Welch's correction. Data are represented as means±SD (*p 0.05, p 0.01, *p 0.001, ****p 0.0001). All experiments were done in triplicates (n=3).

In the studies described herein, the present inventors have shown that fenretinide, zinc, and/or a combination thereof are able to increase the functional cell surface expression of the CFTR ion channel, and notably of the defective F508del-CFTR commonly found in CF patients. It is shown that these compounds exhibit CFTR function potentiation on their own, i.e. in the absence of other CFTR potentiators, but also enhance the effects of known CFTR potentiators such as lumacaftor (VX-809) and genistein. These results provide evidence that fenretinide and/or zinc have the ability to increase the activity of receptors such as ion transporters, and thus may be useful for the treatment of diseases associated with receptor (e.g., ion transporter) dysfunction.

Accordingly, in a first aspect, the present disclosure provides a method for enhancing the activity of a receptor, such as an ion transporter, in a cell, the method comprising contacting the cell with an effective amount of (i) fenretinide, a fenretinide analog, or a salt thereof; (ii) zinc; or (iii) a combination of (i) and (ii). In another aspect, the disclosure provides the use of (i) fenretinide, a fenretinide analog, or a salt thereof; (ii) zinc; or (iii) a combination of (i) and (ii), for enhancing the activity of a receptor, such as an ion transporter, in a cell. In another aspect, the disclosure provides the use of (i) fenretinide, a fenretinide analog, or a salt thereof; (ii) zinc; or (iii) a combination of (i) and (ii), for the manufacture of a medicament for enhancing the activity of a receptor, such as an ion transporter, in a cell. In another aspect, the disclosure provides an agent for enhancing the activity of a receptor, such as an ion transporter, in a cell, wherein the agent is (i) fenretinide, a fenretinide analog, or a salt thereof; (ii) zinc; or (iii) a combination of (i) and (ii).

In an embodiment, the method/use comprises contacting the cell with an effective amount of a combination of zinc and a fenretinide, a fenretinide analog, or a salt thereof. In an embodiment, the receptor (e.g., ion transporter) is a mutated or defective receptor (e.g., ion transporter) having reduced cell surface expression and/or activity relative to the corresponding native receptor (e.g., ion transporter).

In an embodiment, the above-noted above method/use is for enhancing the activity of mutated or defective receptor (e.g., ion transporter) in a cell, and the method/use comprises contacting the cell with an effective amount of (i) fenretinide, a fenretinide analog, or a salt thereof, or (ii) zinc, wherein the receptor/ion transporter is not Cystic Fibrosis Transmembrane Conductance Regulator (CFTR).

The term "receptor" (or "cell surface receptor") as used herein refers to a protein that is embedded in the membranes of cells. Examples of receptor classes include G-protein coupled receptors (GPCRs), enzyme-linked receptors (e.g., receptor tyrosine kinases) and ion transporters (or ion channels).

In an embodiment, the receptor is an ion transporter (or ion channel). Ion channels are transmembrane proteins that allow the flow of ions, both in and out of cells or cellular organelles, following their electrochemical gradients. Because the flux of ions across a membrane results in electrical currents, ion channels play a key role in generating membrane potential and function in diverse cellular activities, such as signal transduction, neurotransmitter release, muscle contraction, hormone secretion, volume regulation, growth, motility, and apoptosis. Ion channels may be classified based on the types of ions that are transported, and include for example chloride channels, potassium channels, calcium channels, sodium channels, proton channels and non-selective cation channels. In an embodiment, the ion channel is a chloride channel. Chloride channels include the CLC family of chloride channels (e.g., CLCN1), the Epithelial Chloride Channel (E-CIC) family, the Chloride Intracellular Ion Channel (CLIC) family as well as certain ATP-binding cassette transporters (ABC transporters) such as CFTR.

In another aspect, the disclosure provides a method for treating a channelopathy in a subject, the method comprising administering to said subject an effective amount of (i) fenretinide, a fenretinide analog, or a pharmaceutically acceptable salt thereof; (ii) zinc; or (iii) a combination of (i) and (ii). In another aspect, the disclosure provides the use of (i) fenretinide, a fenretinide analog, or a pharmaceutically acceptable salt thereof; (ii) zinc; or (iii) a combination of (i) and (ii), for treating a channelopathy in a subject. In another aspect, the disclosure provides the use of (i) fenretinide, a fenretinide analog, or a pharmaceutically acceptable salt thereof; (ii) zinc; or (iii) a combination of (i) and (ii), for the manufacture of a medicament for treating a channelopathy in a subject. In another aspect, the disclosure provides an agent for treating a channelopathy in a subject, wherein the agent is (i) fenretinide, a fenretinide analog, or a pharmaceutically acceptable salt thereof; (ii) zinc; or (iii) a combination of (i) and (ii). In an embodiment, a combination of (i) fenretinide, a fenretinide analog, or a pharmaceutically acceptable salt thereof; and (ii) zinc, is used or administered.

In another aspect, the disclosure provides a method for treating a channelopathy in a subject, the method comprising administering to said subject an effective amount of (i) fenretinide, a fenretinide analog, or a pharmaceutically acceptable salt thereof, or (ii) zinc, wherein the channelopathy is not CF. In another aspect, the disclosure provides the use of (i) fenretinide, a fenretinide analog, or a pharmaceutically acceptable salt thereof, or (ii) zinc, for treating a channelopathy in a subject, wherein the channelopathy is not CF. In another aspect, the disclosure provides the use of (i) fenretinide, a fenretinide analog, or a pharmaceutically acceptable salt thereof, or (ii) zinc, for the manufacture of a medicament for treating a channelopathy in a subject, wherein the channelopathy is not CF. In another aspect, the disclosure provides an agent for treating a channelopathy in a subject, wherein the agent is (i) fenretinide, a fenretinide analog, or a pharmaceutically acceptable salt thereof, or (ii) zinc, and wherein the channelopathy is not CF.

In the studies described herein, it is shown that fenretinide and/or zinc are able to further increase the potentiation of CFTR channel function induced by the CFTR modulators lumacaftor (VX-809) and genistein. Thus, in an embodiment, the method or use further comprises the administration or use of at least one additional ion transporter modulator, e.g., a CFTR modulator. In a further embodiment, the method or use further comprises the administration or use of two or three additional ion transporter modulators, e.g., CFTR modulators. In an embodiment, the subject to whom the (i) fenretinide, a fenretinide analog, or a pharmaceutically acceptable salt thereof, and/or (ii) zinc is administered is a patient previously or currently treated with an ion transporter modulator, e.g., a CFTR modulator (or a combination thereof).

In another aspect, the present disclosure provides a method for improving the ion channel potentiation activity of an ion channel modulator (e.g., CFTR modulator) in a subject, the method comprising administering said ion channel modulator in combination with (i) fenretinide, a fenretinide analog, or a pharmaceutically acceptable salt thereof and/or (ii) zinc. The present disclosure also provides the use of (i) fenretinide, a fenretinide analog, or a pharmaceutically acceptable salt thereof and/or (ii) zinc for improving the ion channel potentiation activity of an ion channel modulator (e.g., CFTR modulator) in a subject. The present disclosure also provides the use of (i) fenretinide, a fenretinide analog, or a pharmaceutically acceptable salt thereof and/or (ii) zinc for the manufacture of a medicament for improving the ion channel potentiation activity of an ion channel modulator (e.g., CFTR modulator) in a subject. The present disclosure also provides an agent for improving the ion channel potentiation activity of an ion channel modulator (e.g., CFTR modulator) in a subject, where the agent is (i) fenretinide, a fenretinide analog, or a pharmaceutically acceptable salt thereof and/or (ii) zinc.

The term "channelopathy" as used herein refers to a disease or condition caused by a dysfunction or defect of an ion channel (or ion transporter). Although defects in ion channels may be caused by either genetic or acquired factors, mutations in genes encoding ion channels, which results in mutated ion channels having impaired channel function, are the most common cause of channelopathies. Thus, in an embodiment, the channelopathy is associated with or caused by a mutated ion channel having reduced levels (e.g., at the cell surface) and/or activity relative to the corresponding native ion channel (e.g., loss-of-function mutations). In a further embodiment, the channelopathy is associated with or caused by a mutated ion channel that is not properly folded and/or that does not properly traffic or localize to the cell surface. In another embodiment, the channelopathy is associated with or caused by a mutated ion channel expressed at the plasma membrane. In an embodiment, the mutation is a heterozygous mutation (the subject has only one defective allele of the gene). In an embodiment, the mutation is a homozygous mutation (the subject has two defective alleles of the gene).

Inflammation has been shown to affect the expression/activity of ion transporters (see, e.g., Michael Eisenhut, *J Inflamm (Lond)*. 2006; 3: 5). Thus, in an embodiment, the dysfunction or defect of the ion transporter is associated with inflammation.

Channelopathies may affect one or more systems, for example the nervous system (e.g., generalized epilepsy with febrile seizures plus, familial hemiplegic migraine, episodic ataxia, and hyperkalemic and hypokalemic periodic paralysis), the cardiovascular system (e.g., long QT syndrome, short QT syndrome, and Brugada syndrome), the respiratory system (e.g., cystic fibrosis), the endocrine system (e.g., neonatal diabetes mellitus, familial hyperinsulinemic hypoglycemia, thyrotoxic hypokalemic periodic paralysis, and familial hyperaldosteronism), and the urinary system (e.g., Bartter syndrome, nephrogenic diabetes insipidus, autosomal-dominant polycystic kidney disease, and hypomagnesemia with secondary hypocalcemia) (see, e.g., June-Bum Kim, *Korean J Pediatr.* 2014 January; 57(1): 1-18).

In an embodiment, the channelopathy is a nervous system channelopathy. FIGS. 7A-7E provide a list of representative channelopathies affecting the nervous system, and the associated defective genes/proteins. Thus, in a further embodiment, the nervous system channelopathy is a disease listed in FIGS. 7A-7E. In an embodiment, the nervous system channelopathy is a skeletal muscle disorder, such as a myotonia, muscle paralysis, Thomsen disease or Becker disease. In an embodiment, the nervous system channelopathy affect neurons and is epilepsy, ataxia, migraine, hyperekplexia, blindness, deafness, or peripheral pain syndrome.

In another embodiment, the channelopathy is a cardiovascular system channelopathy. FIGS. 8A-8C provide a list of representative channelopathies affecting the cardiovascular system, and the associated dysfunctional genes/proteins. Thus, in a further embodiment, the cardiovascular system channelopathy is one of the diseases listed in FIGS. 8A-8C. In an embodiment, the cardiovascular system channelopathy is long QT syndrome (LOTS), bradycardia, Brugada syndrome or tachyarrhythmia.

In another embodiment, the channelopathy is a respiratory system channelopathy. In an embodiment, the respiratory system channelopathy is asthma or CF. Several transient receptor potential (TRP) channels have been associated with bronchial hyper-responsiveness and airway remodeling. ORMDL3, a gene that codes for an endoplasmic reticulum (ER) protein that regulates ER-mediated calcium homeostasis, has been associated with childhood asthma, and reduced expression of sarco/endoplasmic reticulum $Ca^{2+}$-ATPase 2 (SERCA2) has been demonstrated to underlie the abnormal secretory and hyperproliferative phenotype of airway smooth muscle (ASM) in asthma.

In an embodiment, the respiratory system channelopathy is CF. In a further embodiment, CF is caused by a mutation in CFTR. In a further embodiment, the mutation affect or disrupt CFTR protein folding and/or trafficking at the cell surface (often referred to as class II mutations—MacDonald K D et al., *Paediatr Drugs* 2007; 9: 1-10, Welsh M J et al. Cystic fibrosis. Valle D et al. (Eds). OMMBID. The McGraw-Hill Companies Inc. Part 21, chap. 201, 2004). Examples of mutations that affects or disrupt CFTR protein folding and/or trafficking at the cell surface are mutations at positions 508 or 1303 of the CFTR protein. In an embodiment, the mutation at position 1303 of the CFTR protein. In yet a further embodiment, the mutation at position 1303 is a substitution, for example an asparagine to lysine substitution (referred to as N1303K). In an embodiment, the mutation at position 508 of the CFTR protein. In yet a further embodiment, the mutation is a deletion of the phenylalanine residue at position 508 (referred to as phe508del or ΔF508). In another embodiment, the mutation affects the stability or turnover of the CFTR protein at the cell surface (often referred to as class VI mutations). Examples of mutations that affect the stability or turnover of the CFTR protein at the cell surface are 120del23, N287Y, 4326del-ITC, and 4279insA. In another embodiment, the CFTR mutation is 711+3A→G, A455E, D579G, E193K, K1060T, R117C, S945L, 2789+5G→A, A1067T, D1152H, E831X, L206W, R347H, S977F, 3272-26A→G, D110E, D1270N, F1052V, P67L, R352Q 3849+10kbC→T, D110H, E56K, F1074L, R74W or R1070W.

In an embodiment, the channelopathy is an endocrine system channelopathy. FIG. 9 provides a list of representative channelopathies affecting the endocrine system, and the associated dysfunctional genes/proteins. Thus, in a further embodiment, the endocrine system channelopathy is one of the diseases listed in FIG. 9. In an embodiment, the endocrine system channelopathy is an insulin secretory disorder (e.g., hyperinsulinemic hypoglycemia), thyrotoxic periodic paralysis (TPP), or a bone disease (e.g., osteopetrosis).

In an embodiment, the channelopathy is an urinary system channelopathy. FIG. 10 provides a list of representative channelopathies affecting the urinary system (i.e., renal channelopathies), and the associated dysfunctional genes/proteins. Thus, in a further embodiment, the urinary system channelopathy is one of the diseases listed in FIG. 10. In an embodiment, the urinary system channelopathy is autosomal-recessive pseudohypoaldosteronism type 1, nephrogenic diabetes insipidus (NDI), Bartter syndrome, or familial hypomagnesemia with secondary hypocalcemia (HSH).

In an embodiment, the channelopathy is associated with CFTR dysfunction/mutation, for example of a loss-of-function CFTR mutation. In addition to CF, CFTR mutations have been reported in other diseases of mucus clearance including COPD with chronic bronchitis (Raju et al., 2016), asthma, as well as in idiopathic pancreatitis, respiratory conditions such as rhinosinusitis, bronchiectasis and allergic bronchopulmonary aspergillosis, and congenital bilateral absence of the vas deferens (Cohn J A. *J Clin Gastroenterol.* 2005, 39(4 Suppl 2): S70-7; Noone P G, Knowles M R. *Respir Res.* 2001, 2(6): 328-32. Epub 2001 Aug. 9; Ratbi I, et al. *Hum Reprod.* 2007, 22(5): 1285-91. Epub 2007 Feb. 28). In an embodiment, the channelopathy associated with CFTR dysfunction is COPD with chronic bronchitis, asthma, idiopathic pancreatitis, a respiratory condition (e.g., rhinosinusitis, bronchiectasis), or congenital bilateral absence of the vas deferens.

As used herein, the terms "subject" or "patient" are taken to mean warm blooded animals such as mammals, for example, cats, dogs, mice, guinea pigs, horses, bovine cows, sheep and humans. In an embodiment, the subject is a mammal. In a further embodiment, the above-mentioned subject is a human. In an embodiment, the subject is a child. In another embodiment, the subject is an adolescent. In another embodiment, the subject is an adult.

In an embodiment, the subject that is treated suffers from zinc deficiency. The normal reference range for zinc plasma levels is about 10-17 μmol/l (plasma). Thus, a subject suffering from zinc deficiency has zinc levels below about 10 μmol/l, for example about 9.5, 9, 8.5, 8, 7.5 or 7 μmol/1 or less.

Fenretinide and Analogs thereof

Fenretinide (all-trans-N-(4-hydroxyphenyl) retinamide; also referred to as 4-HPR, retinoic acid p-hydroxyanilide), which has CAS registry number 65646-68-6, is a synthetic retinoid of the following formula:

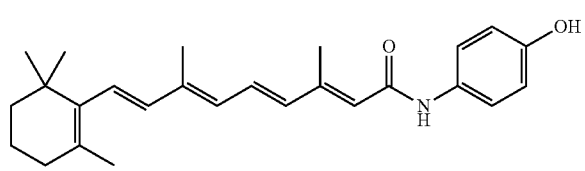 [SMILES: CC1=C(/C=C/C(C)=C/C=C/C(C)=C/C(=O)Nc2ccc(O)cc2)C(C)(C)CCC1]

Functional analogs (and/or metabolites) of fenretinide (i.e. which exhibit the same biological activity as fenretinide) may also be used according to the present disclosure. As used herein, a "fenretinide analog" refers to a compound that shares certain chemical structural features with fenretinide but at the same time comprises one or more modifications thereto, and which exhibits similar biological activity as fenretinide (but may exhibit such activity to a different extent). Examples of analogs of fenretinide that may be used include, but are not limited to, 4-oxo-N-(4-hydroxyphenyl) retinamide (4-oxo-4-HPR), N-(4-methoxyphenyl)retinamide (4-MPR), 4-Hydroxybenzylretinone, C-glycoside and arylamide analogues of N-(4-hydroxyphenyl) retinamide-O-glucuronide, including but not limited to 4-(retinamido)phenyl-C-glucuronide, 4-(retinamido)phenyl-C-glucoside, 4-(retinamido)benzyl-C-xyloside; and retinoyl β-glucuronide analogues such as, for example, 1-β-D-glucopyranosyl) retinamide, 1-(D-glucopyranosyluronosyl) retinamide and bexarotene, described in WO 07/136636, U.S. Patent Application No. 2006/0264514, U.S. Pat. Nos. 5,516,792, 5,663,377, 5,599,953, 5,574,177, Anding et al. (2007) *Cancer Res.* 67: 6270-6277 and Bhatnagar et al. (1991) *Biochem. Pharmacol.* 41: 1471-7. In an embodiment, the fenretinide/fenretinide analog is represented by formula I:

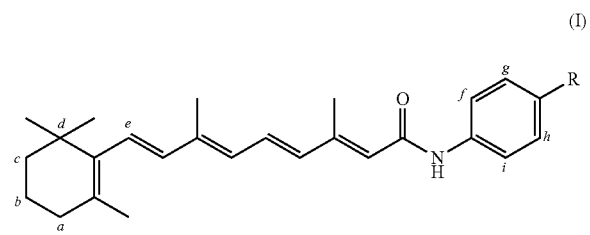

(I)

R is OH, COOH, CH$_2$OH, CH$_2$CH$_2$OH, or CH$_2$COOH;

carbons a-d and f-i are optionally substituted with one or more groups selected from CH$_3$, OH, COOH, (CH$_3$)$_2$ and CH$_2$OH, or any combination thereof, and carbon e is optionally substituted with a C$_1$-C$_3$ alkyl group that is optionally substituted with CH$_3$ and/or OH.

Any salts of fenretinide or fenretinide analogs may also be used in the method or use described herein.

In an embodiment, the above-noted method or use comprises the administration or use of fenretinide or a pharmaceutically acceptable salt thereof. In a further embodiment, the above-noted method or use comprises the administration or use fenretinide.

Zinc

The zinc used in the method and use described herein should be in a physiologically acceptable and assimilable form. A physiologically acceptable source of assimilable zinc is typically a zinc oxide or a salt of zinc with an organic or inorganic acid (salt). Suitable physiologically acceptable salts of zinc with organic acids include salts with orotic acid, aspartic acid, gluconic acid, tartaric acid, citric acid, lactic acid, acetic acid, fumaric acid, maleic acid, malic acid, ascorbic acid, succinic acid, benzoic acid, methanesulphonic acid, ethanesulphonic acid, benzenesulphonic acid, p-toluenesulphonic acid and amino acids, for example glycine, glutamine or cysteine. Suitable physiologically acceptable salts of the above metals with inorganic acids include salts with hydrochloric acid, hydrobromic acid, hydriodic acid, phosphoric acid, diphosphoric acid, nitric acid or sulfuric acid, preferably hydrochloric, hydrobromic, hydroiodic, phosphoric or sulfuric acid. Such salts are available commercially or may be prepared if desired by known methods. In an embodiment, the pharmaceutically acceptable zinc salt is zinc acetate, zinc ascorbate, zinc aspartate, zinc orotate, zinc sulfate, zinc picolinate, zinc glycinate, zinc gluconate, zinc chloride or zinc citrate, preferably zinc sulfate.

Ion Transporter Modulators

The term "ion transporter modulator" refers to an agent that increases the activity of an ion transporter, e.g. by increasing the probability of channel opening or the trafficking of the receptor at the cell surface (e.g., chaperones). Types of ion transporter modulators include ion transporter "potentiators" (which improve ion flow in the channel), ion transporter "correctors" (which improve the folding and/or trafficking of the ion transporter) and ion transporter "amplifiers" or "production corrector" (which increase the amount of ion transporter produced by the cell). In an embodiment, the ion transporter modulator is a CFTR modulator. Examples of CFTR modulators include as the channel potentiators ivacaftor (IVA, VX-770), GLPG2451 and GLPG1837, as well as the CFTR correctors lumacaftor (LUM, VX-809), tezacaftor (VX-661), VX-440, VX-152 and GLPG2222. A single or a combination of two or three ion transporter (e.g., CFTR) modulators may be used. In an embodiment, the CFTR modulator or combination thereof comprises ivacaftor. In another embodiment, the CFTR modulator or combination thereof comprises tezacaftor. In a further embodiment, the CFTR modulator combination comprises ivacaftor and lumacaftor (Orkambi®) or tezacaftor and ivacaftor (Symdeko®). In an embodiment, the combination further comprises a second generation CFTR corrector, for example VX-440 or VX-152.

Dosage

Any suitable amount of fenretinide, fenretinide analog or salt thereof, zinc, and/or ion transporter modulator may be administered to a subject. The dosages will depend on many factors including the mode of administration. Typically, the amount of fenretinide, fenretinide analog or salt thereof, zinc, and/or ion transporter modulator, contained within a single dose will be an amount that effectively prevent, delay or treat the channelopathy without inducing significant toxicity.

For the prevention, treatment or reduction in the severity of a given disease or condition (e.g., a channelopathy), the appropriate dosage of the compound/composition will depend on the type of disease or condition to be treated, the severity and course of the disease or condition, whether the compound/composition is administered for preventive or therapeutic purposes, previous therapy, the patient's clinical history and response to the compound/composition, and the discretion of the attending physician. The fenretinide, fenretinide analog or salt thereof, zinc, and/or ion transporter modulator, is/are suitably administered to the patient at one time or over a series of treatments. Preferably, it is desirable to determine the dose-response curve in vitro, and then in useful animal models prior to testing in humans. The present invention provides dosages for the compounds and compositions comprising same. For example, depending on the type and severity of the disease, about 1 µg/kg to to 1000 mg per kg (mg/kg) of body weight per day. Further, the effective dose may be 0.5 mg/kg, 1 mg/kg, 5 mg/kg, 10 mg/kg, 15 mg/kg, 20 mg/kg/25 mg/kg, 30 mg/kg, 35 mg/kg, 40 mg/kg, 45 mg/kg, 50 mg/kg, 55 mg/kg, 60 mg/kg, 70 mg/kg, 75 mg/kg, 80 mg/kg, 90 mg/kg, 100 mg/kg, 125 mg/kg, 150 mg/kg, 175 mg/kg, 200 mg/kg, and may increase by 25 mg/kg increments up to 1000 mg/kg, or may range between any two of the foregoing values. A typical daily dosage might range from about 1 µg/kg to 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays.

These are simply guidelines since the actual dose must be carefully selected and titrated by the attending physician based upon clinical factors unique to each patient or by a nutritionist. The optimal daily dose will be determined by methods known in the art and will be influenced by factors such as the age of the patient and other clinically relevant factors. In addition, patients may be taking medications for other diseases or conditions. The other medications may be continued during the time that fenretinide, fenretinide analog or salt thereof, zinc, and/or ion transporter modulator is given to the patient, but it is particularly advisable in such cases to begin with low doses to determine if adverse side effects are experienced.

In an embodiment, the amount of fenretinide, fenretinide analog or salt thereof that is administered or used is adjusted to provide a plasma concentration of about 0.5 µM to about 6 µM, for example about 1 µM to about 2.5 or 3 µM, in the subject (at steady state). In an embodiment, the amount of fenretinide, fenretinide analog or salt thereof that is administered or used is about 1 mg to about 500 mg, for example about 5, 10, 15 or 20 mg to about 50, 75, 100, 150, 200 or 250 mg In an embodiment, the amount of zinc that is administered or used is adjusted to provide a plasma concentration of zinc of about 10 µM to about 15 µM in the subject (at steady state). In an embodiment, the amount of zinc that is administered or used is about 1, 1.5 or 2 mg to about 100, 150 or 200 mg of elemental zinc, for example about 2, 2.5 or 3 mg to about 50, 75, 100, 150 mg of elemental zinc, preferably about 2, 3, 4, 5, 6, 7, 8, 9 or 10 mg to about 20, 25, 30, 35, 40, 45, 50, 60, 70, 80, 90, 100, 110, 120, 130, 140 or 150 mg of elemental zinc.

In an embodiment, the zinc administered or used for the treatment of the channelopathy or for enhancing the activity of an ion transporter in a cell is not incorporated into a multivitamin/mineral dietary supplement.

Compositions

The fenretinide, fenretinide analog or salt thereof, zinc, and/or ion transporter modulator, may be combined with one or more optional carriers or excipients to formulate the compound(s) into suitable dosage formulations, such as tablets, capsules (e.g., hard gelatine capsules), caplets, suspensions, powders for suspensions, and the like. Such compositions may be prepared by mixing the active ingredient (e.g., fenretinide and/or zinc) having the desired degree of purity with one or more optional pharmaceutically acceptable carriers, excipients and/or stabilizers in a manner well known in the pharmaceutical art. Supplementary active compounds can also be incorporated into the compositions. The carrier/excipient can be suitable, for example, for oral, intravenous, parenteral, subcutaneous, intramuscular, intranasal or pulmonary (e.g., aerosol) administration (see Remington: *The Science and Practice of Pharmacy*, by Loyd V Allen, Jr, 2012, $22^{nd}$ edition, Pharmaceutical Press; *Handbook of Pharmaceutical Excipients*, by Rowe et al., 2012, $7^{th}$ edition, Pharmaceutical Press). Therapeutic formulations are prepared using standard methods known in the art.

An "excipient," as used herein, has its normal meaning in the art and is any ingredient that is not an active ingredient (drug) itself. Excipients include for example binders, lubricants, diluents, fillers, thickening agents, disintegrants, plasticizers, coatings, barrier layer formulations, lubricants, stabilizing agent, release-delaying agents and other components. "Pharmaceutically acceptable excipient" as used herein refers to any excipient that does not interfere with effectiveness of the biological activity of the active ingredients and that is not toxic to the subject, i.e., is a type of excipient and/or is for use in an amount which is not toxic to the subject. Excipients are well known in the art, and the present system is not limited in these respects. In certain embodiments, the composition includes excipients, including for example and without limitation, one or more binders (binding agents), thickening agents, surfactants, diluents, release-delaying agents, colorants, flavoring agents, fillers, disintegrants/dissolution promoting agents, lubricants, plasticizers, silica flow conditioners, glidants, anti-caking agents, anti-tacking agents, stabilizing agents, anti-static agents, swelling agents and any combinations thereof. As those of skill would recognize, a single excipient can fulfill more than two functions at once, e.g., can act as both a binding agent and a thickening agent. As those of skill will also recognize, these terms are not necessarily mutually exclusive.

Examples of matrix materials, fillers, or diluents include, without limitation, lactose, mannitol, xylitol, microcrystalline cellulose, dibasic calcium phosphate (anhydrous and dihydrate), starch, and any combination thereof.

Examples of disintegrants include, without limitation, sodium starch glycolate, sodium alginate, carboxy methyl cellulose sodium, methyl cellulose, and croscarmellose sodium, and crosslinked forms of polyvinyl pyrrolidone such as those sold under the trade name CROSPOVIDONE® (available from BASF Corporation), and any combination thereof.

Examples of binders include, without limitation, methyl cellulose, microcrystalline cellulose, starch, and gums such as guar gum, tragacanth, and any combination thereof.

Examples of lubricants include, without limitation, magnesium stearate, calcium stearate, stearic acid, and any combination thereof.

Examples of glidants include, without limitation, metal silicates, silicon dioxides, higher fatty acid metal salts, metal oxides, alkaline earth metal salts, and metal hydroxides.

Examples of preservatives include, without limitation, sulfites (an antioxidant), benzalkonium chloride, methyl paraben, propyl paraben, benzyl alcohol, sodium benzoate, and any combination thereof.

Examples of suspending agents or thickeners, without limitation, include xanthan gum, starch, guar gum, sodium alginate, carboxymethyl cellulose, sodium carboxymethyl cellulose, methyl cellulose, hydroxypropyl methyl cellulose, polyacrylic acid, silica gel, aluminum silicate, magnesium silicate, titanium dioxide, and any combination thereof.

Examples of anti-caking agents or fillers, without limitation, include silicon oxide, lactose, and any combination thereof.

Examples of solubilizers include, without limitation, ethanol, propylene glycol, polyethylene glycol, and any combination thereof.

Examples of antioxidants include, without limitation, phenolic-based antioxidants such as butylated hydroxyanisole (BHA), butylated hydroxytoluene (BHT), tert-butyl-hydroquinone (TBHQ), 4-hydroxymethyl-2,6-di-tert-butylphenol (HMBP), 2,4,5-trihydroxy-butyrophenone (THBP), propyl gallate (PG), triamyl gallate, gallic acid (GA), α-Tocopherol (vitamin E), tocopherol acetate, reducing agents such as L-ascorbic acid (vitamin C), L-ascorbyl palmitate, L-ascorbyl stearate, thioglycolic acid (TGA), ascorbyl palmitate (ASP), sulphite-based antioxidants such as sodium sulphite, sodium metabisulphite, sodium bisulphite and thioglycerol and other agents such as disodium ethylenediamine tetraacetate (EDTA), sodium pyrophosphate, sodium metaphosphate, methionine, erythorbic acid and lecithin, and any combination thereof. In an embodiment, the formulation comprises a combination of antioxidants. In an embodiment, the formulation comprises a combination of BHA and BHT. In an embodiment, the formulation comprises ascorbic acid.

Another class of excipients is surfactants, optionally present from about 0 to about 10 wt %. Suitable surfactants include, without limitation, fatty acid and alkyl sulfonates; commercial surfactants such as benzalkonium chloride (HYAMINE® 1622, available from Lonza, Inc., Fairlawn, N.J.); dioctyl sodium sulfosuccinate (DOCUSATE SODIUM, available from Mallinckrodt Spec. Chem., St. Louis, Mo.); polyoxyethylene sorbitan fatty acid esters (TWEEN®, available from ICI Americas Inc., Wilmington, Del.; LIPOSORB® O-20, available from Lipochem Inc., Patterson N.J.; CAPMUL™. POE-0, available from Abitec Corp., Janesville, Wis.); and natural surfactants such as sodium taurocholic acid, 1-palmitoyl-2-oleoyl-sn-glycero-3-phosphocholine, lecithin, and other phospholipids and mono- and diglycerides, and any combination thereof. Such materials can be employed to increase the rate of dissolution by, for example, facilitating wetting, or otherwise increase the rate of drug release from the dosage form.

Other conventional excipients, including pigments, lubricants, flavorants, humectants, solution retarding agents, absorption accelerators, wetting agents, absorbents, and other ones well-known in the art, may be employed in the compositions of this invention. For example, excipients such as pigments, lubricants, flavorants, and so forth may be used for customary purposes and in typical amounts without adversely affecting the properties of the compositions.

Other components commonly added to pharmaceutical compositions include, e.g., inorganic salts such as sodium chloride, potassium chloride, calcium chloride, sodium phosphate, potassium phosphate, sodium bicarbonate; and organic salts such as sodium citrate, potassium citrate, sodium acetate, etc.

In an embodiment, the fenretinide, fenretinide analog or salt thereof is present in the composition as an amorphous solid dispersion as described in U.S. Patent Publication No. 2017/0189356 A1, which is incorporated by reference in its entirety.

An "amorphous solid dispersion" refers to a dispersion in which at least a major portion (i.e. more than 50%) of the fenretinide, fenretinide analog, or salt thereof in the dispersion is in amorphous form. By "amorphous" is meant that the fenretinide, fenretinide analog, or salt thereof is in a non-crystalline state. In embodiments, at least 55, 60, 65, 70, 75, 80, 85, 90% or 95% of the fenretinide, fenretinide analog, or salt thereof (by weight) in the dispersion is in the amorphous form.

"Solid dispersion" refers to a solid material, in which a drug (e.g., fenretinide) is dispersed in the solid matrix polymer. Such solid dispersions are also referred to in the art as "molecular dispersions" or "solid solutions" of the drug in the polymer. Solid dispersions may be obtained by various techniques, for example fast evaporation, spray-drying, precipitation or melt extrusion (e.g., hot melt extrusion, HME). In an embodiment, the solid dispersion is obtained by spray-drying (spray-dried solid dispersion).

Examples of "matrix polymers", also referred to in the field as "concentration-enhancing polymers" or "dispersion polymers", which may be suitable for use in the present invention, are discussed in detail in for example U.S. Pat. Nos. 7,780,988 and 7,887,840. The matrix polymer can be any pharmaceutically acceptable polymer that, once co-processed with the fenretinide, fenretinide analog, or salt thereof, functions to maintain the fenretinide/fenretinide analog in amorphous form.

Examples of polymers that may be suitable for use with the present invention comprise non-ionizable (neutral) non-cellulosic polymers. Exemplary polymers include: vinyl polymers and copolymers having at least one substituent selected from hydroxyl, alkylacyloxy, and cyclicamido; polyvinyl alcohols that have at least a portion of their repeat units in the unhydrolyzed (vinyl acetate) form; polyvinyl alcohol polyvinyl acetate copolymers; polyvinyl pyrrolidone; and polyethylene polyvinyl alcohol copolymers; and polyoxyethylene-polyoxypropylene copolymers.

Other examples of polymers that may be suitable for use with the present invention comprise ionizable non-cellulosic polymers. Exemplary polymers include: carboxylic acid-functionalized vinyl polymers, such as the carboxylic acid functionalized polymethacrylates and carboxylic acid functionalized polyacrylates such as the EUDRAGIT® series, amine-functionalized polyacrylates and polymethacrylates; proteins such as gelatin and albumin; and carboxylic acid functionalized starches such as starch glycolate.

Other examples polymers that may be suitable for use with the present invention comprise nonionizable cellulosic polymers that may be used as the polymer include: hydroxypropyl methyl cellulose acetate, hydroxypropyl methyl cellulose (HPMC), hydroxypropyl cellulose, methyl cellulose, hydroxyethyl methyl cellulose, hydroxyethyl cellulose acetate, hydroxyethyl ethyl cellulose, and the like.

While specific polymers have been discussed as being suitable for use in the dispersions formable by the present invention, blends of such polymers may also be suitable. Thus, the term "matrix polymer" is intended to include blends of polymers in addition to a single species of polymer.

In an embodiment, the matrix polymer comprises polyvinylpyrrolidone. In another embodiment, the matrix polymer is a polyvinylpyrrolidone, for example polymers sold under the trade-name Plasdone® (povidones), polyvinylpyrrolidone K12, polyvinylpyrrolidone K17, polyvinylpyrrolidone K25, polyvinylpyrrolidone K30 or polyvinylpyrrolidone K90.

In an embodiment, the ratio of the fenretinide, fenretinide analog, or salt thereof/matrix polymer is from about 1:5 to about 5:1, in further embodiments about 1:4 to about 4:1, about 1:3 to about 3:1, about 1:2 to about 2:1 or about 1.5:1 to about 1:1.5, by weight. In an embodiment, the solid dispersion comprises between about 30 to about 50% of the fenretinide, fenretinide analog, or salt thereof, and between about 50 to about 70% of matrix polymer. In another embodiment, the solid dispersion comprises between about 40% of the fenretinide, fenretinide analog, or salt thereof, and about 60% of matrix polymer, by weight.

In an embodiment, the solid dispersion comprises one or more additives. Additives that may be suitable for use with the present invention comprise antioxidant agents. Exemplary antioxidants include: L-ascorbic acid (vitamin C), propyl gallate, sodium sulfite, sodium metabisulfite, sodium bisulfite, thioglycerol, thioglycollic acid, tocopherols and tocotrienols, butylated hydroxyanisole (BHA), butylated hydroxytoluene (BHT) or any combination thereof. In an embodiment, the matrix polymer or solid dispersion comprises BHA and/or BHT as antioxidant agent(s). In an embodiment, the matrix polymer or solid dispersion comprises BHA and BHT as antioxidant agents. In an embodiment, the matrix polymer comprises L-ascorbic acid as antioxidant agent. In an embodiment, the antioxidant agent(s) is/are present in an amount of about 0.01% to about 5%, in further embodiments in an amount of about 0.1% to about 5%, about 0.2% to about 4%, 0.5% to about 3% or 0.5% to about 2%.

The amorphous solid dispersion of fenretinide, fenretinide analog, or salt thereof may be combined with one or more optional excipients as described above.

In an embodiment, the amorphous solid dispersion of fenretinide, fenretinide analog, or salt thereof is combined with a disintegrant, for example a cross-linked sodium carboxymethylcellulose e.g., croscarmellose (Solutab®). Other examples of disintegrants include corn starch, potato starch, sodium carboxymethylcellulose, sodium starch glycolate, sodium croscarmellose, crospovidone, and any combination thereof. In an embodiment, the disintegrant is present in an amount from about 2 to about 10% by weight, for example from about 3 to about 8% or about 4 to about 6% by weight.

In an embodiment, the amorphous solid dispersion of fenretinide, fenretinide analog, or salt thereof is combined with a lubricant, for example magnesium stearate. Other examples of lubricants include talc, silicon dioxide, stearic acid, and sodium stearyl fumarate. In an embodiment, the lubricant is present in an amount from about 0.5 to about 2% by weight, for example from about 0.8 to about 1.2% or about 1% by weight.

In an embodiment, the amorphous solid dispersion of fenretinide, fenretinide analog, or salt thereof is combined with a filler or diluent, for example microcrystalline cellulose (Avicel®, such as Avicel®PH-102) and/or calcium hydrogen phosphate dehydrate (Encompress®). Other examples of fillers or diluents include crystalline cellulose, cellulose derivatives, acacia, corn starch, lactose, mannitol, sugars, calcium phosphate, calcium carbonate, gelatins, and any combination thereof. In an embodiment, the filler or diluent is present in an amount from about 20 to about 45% by weight, for example from about 30% to about 40% by weight, e.g., about 35%.

In an embodiment, the amorphous solid dispersion of fenretinide, fenretinide analog, or salt thereof is combined one or more antioxidants, for example butylated hydroxyanisole (BHA), butylated hydroxytoluene (BHT), citric acid, sodium metabisulfite, alpha-tocopherol and/or L-ascorbic acid.

In certain embodiments, the amorphous solid dispersion as disclosed herein is formulated as an oral dosage formulation. Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an elixir or syrup, or as pastilles (using an inert matrix, such as gelatin and glycerin, or sucrose and acacia), and the like, each containing a predetermined amount of an active ingredient. A composition may also be administered as a bolus, electuary, or paste.

In an embodiment, the oral dosage formulation is a tablet. A tablet may be made by compression or molding, optionally with one or more accessory ingredients. Compressed tablets may be prepared using binder, lubricant, inert diluent, preservative, disintegrant, surface-active or dispersing agent. Molded tablets may be made by molding in a suitable machine a mixture of the powdered inhibitor(s) moistened with an inert liquid diluent.

In some embodiments of the oral dosage formulation as disclosed herein, the amorphous solid dispersion is present in an amount of from about 10 to about 90%, about 20 to about 80%, about 30 to about 60% or about 45 to about 55% by weight, or another range within the values provided herein.

In an embodiment, in the method or use described herein based on a combination of ingredients, the (i) fenretinide, fenretinide analog, or salt thereof; (ii) zinc, and/or (iii) ion transporter modulator are formulated into separate compositions, i.e. are administered/used separately. The combination of agents and/or compositions may be administered or co-administered (e.g., consecutively, simultaneously, at different times) in any conventional dosage form. Co-administration in the context of the present invention refers to the administration of more than one therapeutic in the course of a coordinated treatment to achieve an improved clinical outcome. Such co-administration may also be coextensive, that is, occurring during overlapping periods of time. For example, a first agent (e.g., fenretinide, fenretinide analog, or salt thereof) may be administered to a patient before, concomitantly, before and after, or after a second active agent (e.g., zinc) is administered. Similarly, the ion transporter modulator may be administered to a patient before, concomitantly, before and after, or after the first and/or second active agent(s).

In another embodiment, the (i) fenretinide, fenretinide analog, or salt thereof; and (ii) zinc, are formulated into the same composition and thus administered/used at the same time. In an embodiment, the composition comprising the amorphous solid dispersion of fenretinide, fenretinide analog, or salt thereof as disclosed herein. In an embodiment, the ion transporter modulator is formulated in the same composition as the (i) fenretinide, fenretinide analog, or salt thereof; and (ii) zinc. In another embodiment, the ion transporter modulator is formulated in a different composition than the (i) fenretinide, fenretinide analog, or salt thereof; and (ii) zinc.

In an embodiment, the dose of the (i) fenretinide, fenretinide analog, or salt thereof; (ii) zinc, and/or (iii) ion transporter modulator that is used/administered in the methods and uses described herein is a suboptimal dose. "Suboptimal dose" as used herein refers to a dose of one of the compounds of the combination described herein, which, when used in the absence of the compound of the combination, results in a biological effect of 50% or less, in an embodiment of 40% or less, in a further embodiment of 30% or less, in a further embodiment of 20% or less, in a further embodiment of 10% or less. As such, use of a combination of the compounds described herein, where one or more compounds in the combination is used at a suboptimal dose, may achieve increased efficacy/biological effect relative to using the compound(s) in the absence of the other(s), at a comparable suboptimal dose.

In an embodiment, the (i) fenretinide, fenretinide analog, or salt thereof; (ii) zinc, and/or (iii) ion transporter modulator exhibit a synergistic effect. A synergistic effect is achieved when a biological effect of the combined agents is greater than the theoretical sum of the effect of each agent in the absence of the other. One potential advantage of combination therapy with a synergistic effect is that lower dosages (e.g., a suboptimal dose) of one or more of the agents or therapies may be used in order to achieve high therapeutic activity with low toxicity. In an embodiment, the combination therapy results in at least a 5% increase in the effect as compared to the predicted theoretical additive effect of the agents. In a further embodiment, the combination therapy results in at least a 10% increase in the effect as compared to the predicted theoretical additive effect of the agents. In a further embodiment, the combination therapy results in at least a 20% increase in the effect as compared to the predicted theoretical additive effect of the agents. In a further embodiment, the combination therapy results in at least a 30% increase in the effect as compared to the predicted theoretical additive effect of the agents. A further advantage of using the drugs in combination is that efficacy may be achieved in situations where either agent alone would not have a significant effect.

Kits and Packages

The present disclosure also relates to kits or packages comprising one or more of (i) a fenretinide, fenretinide analog, or salt thereof; (ii) zinc, and/or (iii) an ion transporter modulator, such as a CFTR modulator. In an embodiment, the kit or package comprises at least two of items (i)-(iii) defined above. In an embodiment, the kit comprises (i) a fenretinide, fenretinide analog, or salt thereof; and (ii) zinc. In another embodiment, the kit comprises (i) a fenretinide, fenretinide analog, or salt thereof; and (iii) an ion transporter modulator. In another embodiment, the kit comprises (i) a fenretinide, fenretinide analog, or salt thereof; (ii) zinc; and (ii) an ion transporter modulator. In another embodiment, the kit comprises (i) zinc; and (ii) an ion transporter modulator. In another embodiment, the kit comprises at least two ion transporter modulators, for example at least two CFTR modulators (e.g., ivacaftor (IVA, VX-770), GLPG2451, GLPG1837, lumacaftor (LUM, VX-809), tezacaftor (VX-661), VX-440, VX-152 or GLPG2222). In an embodiment, the CFTR modulator or at least two CFTR modulators comprise ivacaftor. In another embodiment, the CFTR modulator or at least two CFTR modulators comprise tezacaftor. In a further embodiment, the at least two CFTR modulators comprise ivacaftor and tezacaftor.

The kit or package may further comprise one or more containers, physiologically acceptable diluents, devices for administering the agents, etc. The kit or package may also comprise instructions and/or informational material. Informational material included in the kits can be descriptive, instructional, marketing or other material that relates to the methods/uses described herein. For example, the informational material of the kit or package can contain contact information, e.g., a physical address, email address, website, or telephone number, where a user of the kit or package can obtain substantive information about the agents comprises in the kit or package, information concerning the administration of the agents, etc.

In an embodiment, the kit or package is for enhancing the activity of mutated or defective ion transporter in a cell, treating a channelopathy in a subject, and/or improving the ion channel potentiation activity of an ion channel modulator (e.g., CFTR modulator) in a subject.

MODE(S) FOR CARRYING OUT THE INVENTION

The present invention is illustrated in further details by the following non-limiting examples.

EXAMPLE 1

Effect of Fenretinide and Zinc Treatment on the Fatty Acid Levels and cPLA$_2$ Activity in Lung Epithelial Cells The effect of fenretinide (Fen) and/or zinc ($Zn^{2+}$) ions on the lipid metabolism in human airway epithelial cells was assessed the modulation of cytoplasmic phospholipases (cPLA$_2$) activity. cPLA$_2$ activity, as evaluated by colorimetric assay, was decreased following fenretinide treatment in a time dependent fashion, starting 24h after treatment (FIG. 1). Also, zinc was shown to potentiate the effect of fenretinide at 24h and 48h, and to significantly increase cPLA$_2$ activity at 72h in the absence of fenretinide.

Figure 2A:
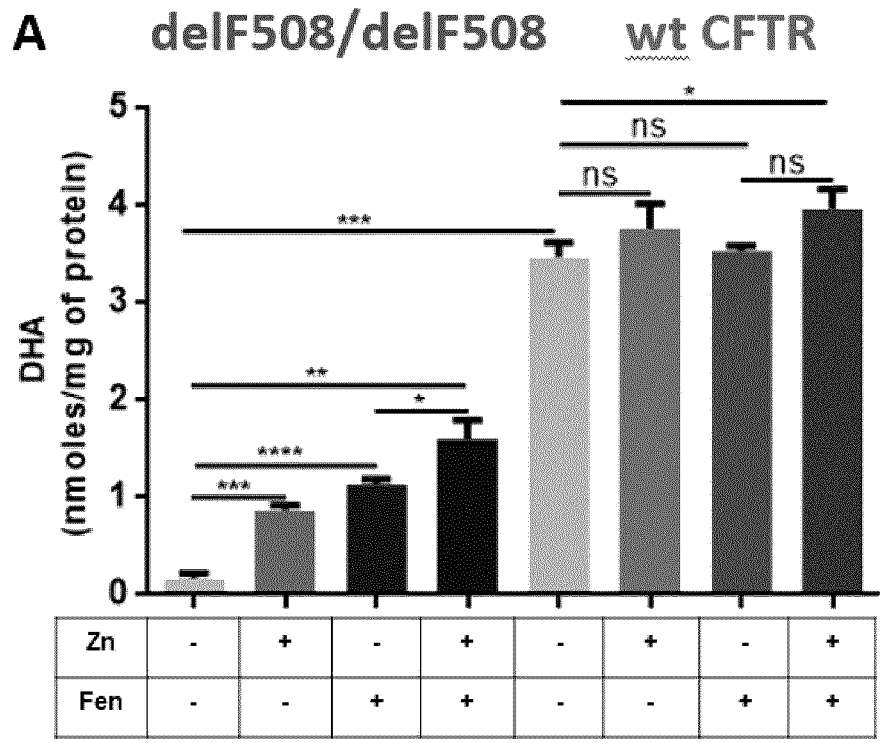
FIGS. 2A-C are graphs showing the effect of fenretinide, $Zn^{2+}$ treatment on the level of DHA (FIG. 2A), AA (FIG. 2B) and their ratio (FIG. 2C) in lung epithelial cells overexpressing a mutant form of CFTR (CFTR-delF508) or native CFTR (wt CFTR). Lung epithelial cells grown as 80% confluent monolayer of were treated for 72h with 1.25 µM fenretinide and/or 12.5 µM zinc sulfate. The levels of AA and DHA were assessed as previously described in Guilbault et al. 2008, 2009. All statistical analyses were performed using GraphPad™ software (GraphPad, San Diego, Calif., USA). Statistical significance of differences was evaluated using unpaired t-test with Welch's correction. Data are represented as means±SD (*p≤0.05, p≤0.01, *p≤0.001, ****p≤0.0001). All experiments were done in triplicates (n=3).
Figure 2B:
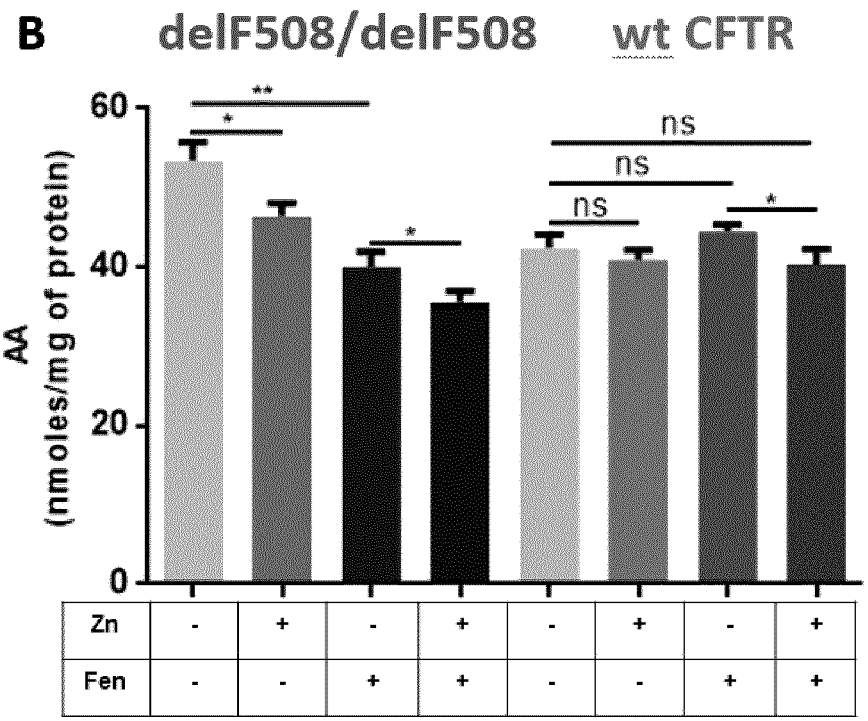
Figure 2C:
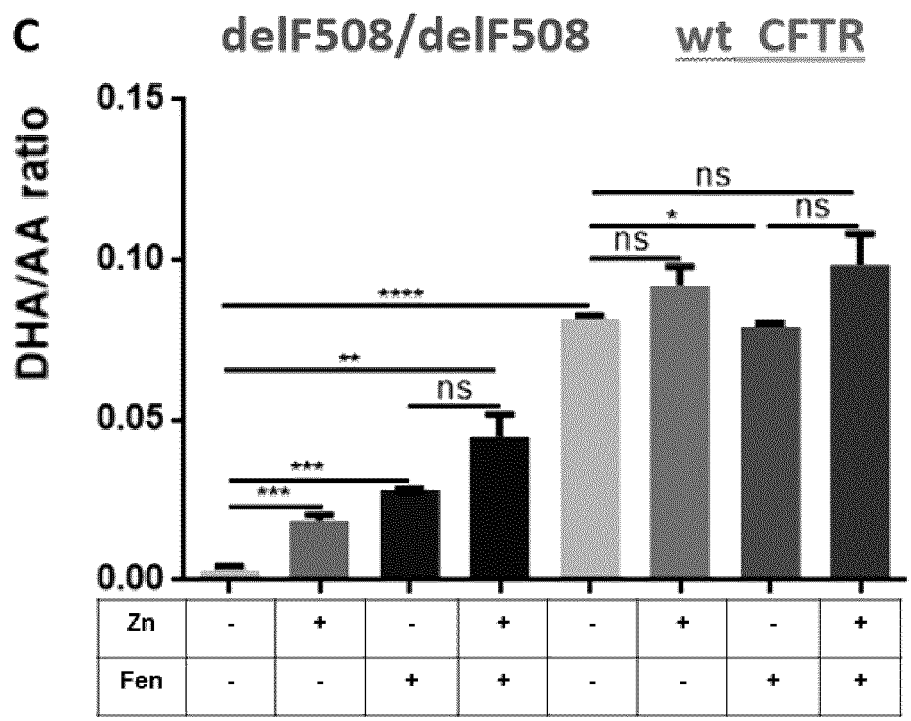

It was next assessed whether fenretinide and zinc modulate the levels of omega-3 (docosahexaenoic acid, DHA) and omega-6 (arachidonic acid, AA) fatty acids in airway epithelial cells overexpressing the delF508 mutated form of CFTR (delF508/delF508) or native CFTR (wt CFTR). The results depicted in FIG. 2A show that fenretinide alone, zinc alone, and the combination of fenretinide and zinc induce a significant increase (relative to untreated cells) in DHA levels in cells overexpressing the delF508 CFTR, whereas only the treatment with the fenretinide+zinc combination was able to do so in cells overexpressing native CFTR. For AA levels, all treatments led to a significant decrease in AA levels in delF508 CFTR-expressing cells (relative to untreated cells), but not in native CFTR-expressing cells. Interestingly, native CFTR-expressing cells treated with fenretinide+zinc had significantly lower AA levels relative to corresponding cells treated with fenretinide alone (FIG. 2B). Consistent with the results obtained for DHA and AA levels, fenretinide alone, zinc alone, and the combination of fenretinide and zinc induce a significant increase (relative to untreated cells) in the DHA/AA ratio in cells overexpressing the delF508 CFTR, but not in cells overexpressing native CFTR.

EXAMPLE 2

Effect of Fenretinide and Zinc Treatment on CFTR Functional Expression

Figure 3A:
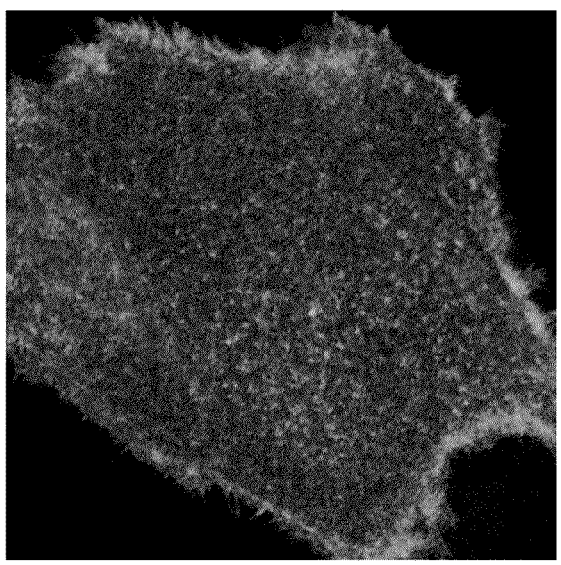
FIGS. 3A-E are confocal images of GFP-wt-CFTR expressed at the plasma membrane of pHBE cells under control conditions (Ctr) (FIG. 3A); after 10-20 min treatment with 2 µM Thapsigargin (FIG. 3B); after treatment with 1.25 µM Fenretinide (FIG. 3C); after treatment with 1.25 µM Fenretinide and Thapsigargin (same conditions as above) (FIG. 3D); or after treatment with 1.25 µM Fenretinide+Thapsigargin (same conditions as above)+Amitriptyline (13 µM for 40 min) (FIG. 3E).
Figure 3B:
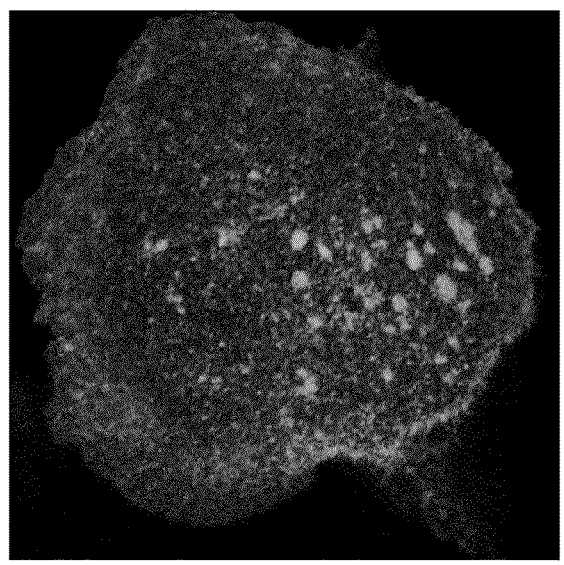
Figure 3C:
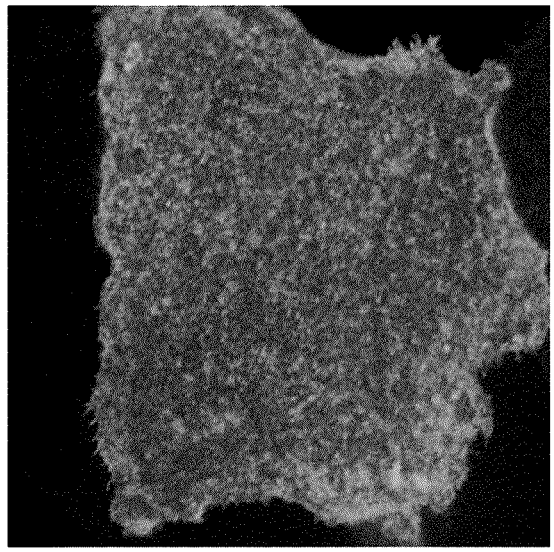
Figure 3D:
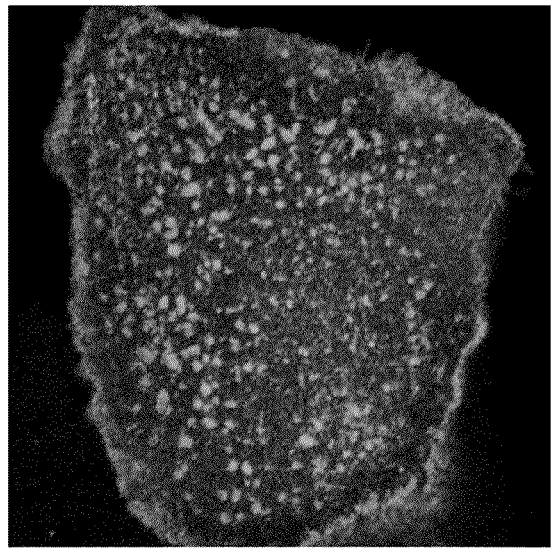
Figure 3E:
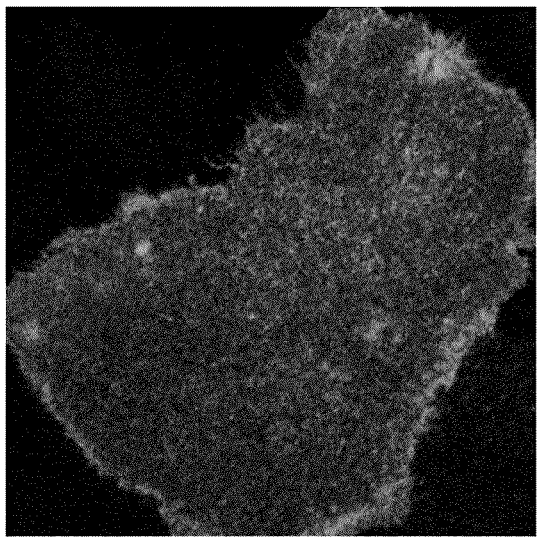
Figure 3F:
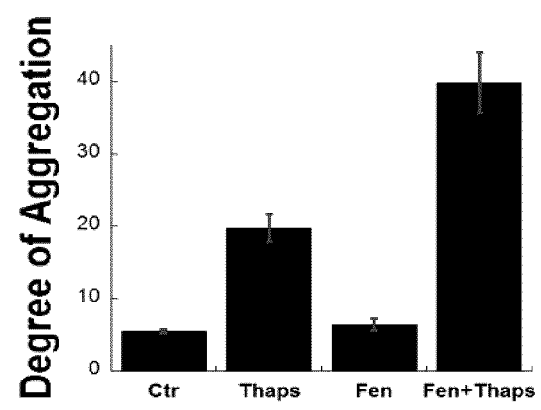
FIG. 3F is a graph showing the quantification of CFTR aggregation and accumulation at the cell surface under control conditions (Ctr), after treatment with Thapsigargin (Thaps), after treatment with Fenretinide (Fen), and after treatment with Fenretinide and Thapsigargin (Fen+Thaps).

It was next tested whether fenretinide and/or zinc could have an effect on the ability of native CFTR-expressing epithelial cells to transport chloride. CFTR is known to become localized in relatively stable platforms during viral infection (Abu-Arish et al., 2015). The formation of such platforms expressing CFTR was measured following treatment with fenretinide. The Image Correlation Spectroscopy technique was used to measure the degree of aggregation of GFP-wt-CFTR at the plasma membrane of primary human bronchial epithelial cells. The degree of aggregation is proportional to the mean number of CFTR channels per cluster or platform. Confocal images of CFTR at the plasma membrane were collected for analysis under control (Ctr), thapsigargin (Thaps), fenretinide (Fen) or a combination of Fen+Thaps. Cells were pretreated or not with fenretinide at 1.25 µM for 24 h before imaging whereas Thaps (2 µM) exposures were acute (10-20 min). As shown in FIGS. 3A-3F, although fenretinide alone did not affect CFTR clustering (FIG. 3C, 3F) and thapsigargin itself (which is known to increase cytoplasmic calcium and induce ER stress as occurs during the unfolded protein response) induces some CFTR platforms (FIG. 3B, 3F), pretreating primary bronchial epithelial cells with fenretinide prior to thapsigargin treatment caused a significant increase in the number and size of these platforms (FIG. 3D, 3F). Induction of platform formation by fenretinide+thapsigargin was inhibited in the presence of the acid sphingomyelinase inhibitor Amitriptyline (Ami) (FIG. 3E), indicating that the effect of fenretinide+thapsigargin on the formation of CFTR platforms is ceramide-dependent.

The association between aggregation of CFTR protein at the apical plasma membrane and the functional improvement of CFTR chloride channel functions was tested. To do so, Ussing Chambers were used to measure F508del-CFTR and wt-CFTR functional expression as short-circuit current across polarized bronchial epithelial cells in response to forskolin (FSK). As shown in FIGS. 4A-4B, the combination Fen+Zn caused a 57% ($p<0.005$, 4 experiments, n=12-14 filter/condition) and 33% ($p<0.001$, 5 experiments, n=15 filter/condition) increase in F508del-CFTR and wt-CFTR channel-mediated current, respectively.

It was next tested whether fenretinide and/or zinc could potentiate the effect of known CFTR modulators, namely lumacaftor (VX-809) that is known to act as a chaperone during protein folding and increases the number of CFTR proteins that are trafficked to the cell surface, as well as genistein (another CFTR potentiator whose activity is similar to that of the CFTR potentiator ivacaftor (VX-770)). The results depicted in FIG. 5 demonstrate that the Fen+Zn combination caused a 60% and 52% ($p<0.0005$, 6 experiments, n=22-32 filter/condition) increases in F508del-CFTR channel conductance above the correction by VX-809 alone in response to FSK and FSK+Gen, respectively. Furthermore, treatment with Fen alone led to a significant increase ($p<0.02$) in F508del-CFTR channel function.

Figure 6:
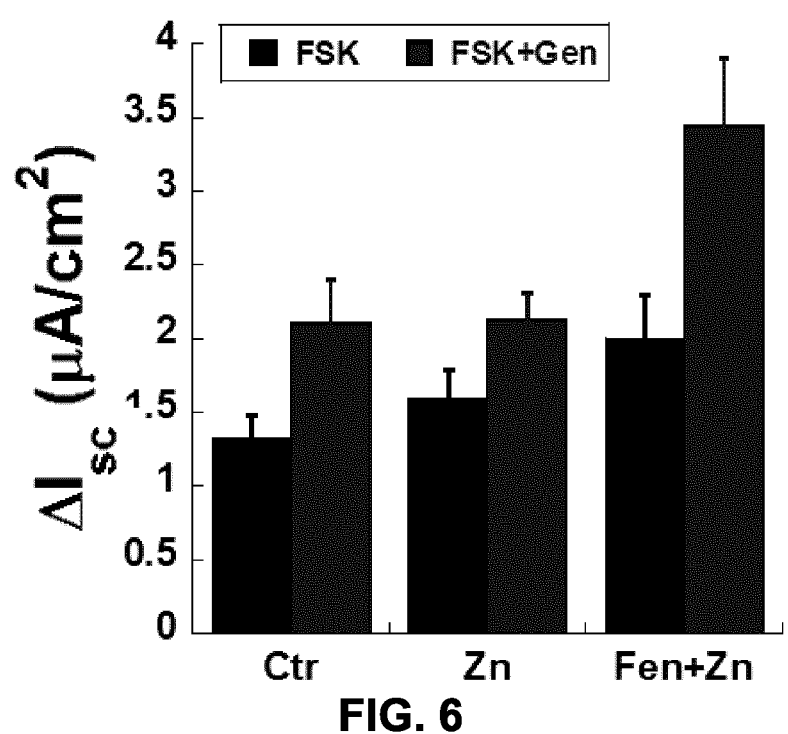
FIG. 6 is a graph showing the effect of Zinc and/or Fenretinide treatment on F508del-CFTR mediated secretion in the absence of VX-809. Ussing Chambers were used to measure F508del-CFTR functional expression as short-circuit current across polarized and basally permeabilized bronchial epithelial cells in response to forskolin (FSK) or forskolin+genistein (FSK+Gen). Cells were treated basally or not with 1.25 µM Fenretinide (Fen) and/or 12.5 µM Zinc (Zn) for 3 days.

Additional experiments performed on cells not treated with the CFTR potentiator VX-809 showed that the Fen+Zn combination led to a significant increase in F508del-CFTR response to FSK and FSK+Gen (52% and 63%, respectively; $p<0.05$, 2 experiments, n=4-6 filter/condition) (FIG. 6). Thus, in addition to enhancing the effects of known CFTR potentiators, the Fen+Zn combination also exhibits CFTR function potentiation in the absence of other CFTR potentiators.

Although the present invention has been described hereinabove by way of specific embodiments thereof, it can be modified, without departing from the spirit and nature of the subject invention as defined in the appended claims. In the claims, the word "comprising" is used as an open-ended term, substantially equivalent to the phrase "including, but not limited to". The singular forms "a", "an" and "the" include corresponding plural references unless the context clearly dictates otherwise.

What is claimed is:

1. A method for enhancing the activity of Cystic Fibrosis Transmembrane Conductance Regulator (CFTR) ion transporter in a cell under inflammatory conditions, the method comprising contacting the cell with an effective amount of:
    (a) a combination of (i) fenretinide, a fenretinide analog, or a salt thereof; and (ii) a CFTR modulator; or
    (b) a combination of (i) fenretinide, a fenretinide analog, or a salt thereof; (ii) zinc; and (iii) a CFTR modulator.

2. The method of claim 1, wherein the CFTR ion transporter is a mutated or defective CFTR ion transporter having reduced cell surface expression and/or activity relative to the corresponding native CFTR ion transporter.

3. The method of claim 2, wherein the CFTR ion transporter is a mutated CFTR ion transporter.

4. The method of claim 3, wherein the mutated CFTR ion transporter comprises a mutation at position 508 of the CFTR protein.

5. A method for treating a channelopathy caused by a mutated or defective Cystic Fibrosis Transmembrane Conductance Regulator (CFTR) ion transporter having reduced cell surface expression and/or activity relative to the corresponding native CFTR ion transporter in a subject, the method comprising administering to said subject an effective amount of (a) (i) fenretinide, a fenretinide analog, or a pharmaceutically acceptable salt thereof; (ii) a physiologically acceptable source of assimilable zinc; or (iii) a combination of (i) and (ii); and (b) a CFTR modulator, wherein the channelopathy is associated with inflammation.

6. The method of claim 5, wherein the channelopathy is cystic fibrosis (CF), chronic obstructive pulmonary disease (COPD), asthma, idiopathic pancreatitis, rhinosinusitis, bronchiectasis, or congenital bilateral absence of the vas deferens.

7. The method of claim 5, wherein the channelopathy is a respiratory system channelopathy.

8. The method of claim 7, wherein the channelopathy is CF.

9. The method of claim 5, wherein said subject suffers from zinc deficiency.

10. The method of claim 5, wherein said method comprises administering an effective amount of a combination of (i) fenretinide, a fenretinide analog, or a pharmaceutically acceptable salt thereof; (ii) a physiologically acceptable source of assimilable zinc and (iii) a CFTR modulator.

11. The method of claim 5, wherein said physiologically acceptable source of assimilable zinc is zinc oxide or a pharmaceutically acceptable zinc salt.

12. The method of claim 11, wherein said pharmaceutically acceptable zinc salt is zinc sulfate.

13. The method of claim 5, wherein the effective amount of fenretinide, fenretinide analog or salt thereof that is administered provides a plasma concentration of the fenretinide, fenretinide analog or salt thereof of about 0.5 µM to about 6µM.

14. The method of claim 5, wherein the effective amount of fenretinide, fenretinide analog or salt thereof that is administered is about 1 mg to about 500 mg.

15. The method of claim 5, wherein the effective amount of physiologically acceptable source of assimilable zinc that is administered provides a plasma concentration of zinc of about 10 µM to about 15 µM in the subject.

16. The method of claim 5, wherein the effective amount of physiologically acceptable source of assimilable zinc that is administered comprises about 1 mg to about 200 mg of elemental zinc.

17. The method of claim 5, wherein the (i) fenretinide, fenretinide analog or salt thereof is present in amorphous form in a solid dispersion comprising a matrix polymer.

18. The method of claim 17, wherein the matrix polymer is a polyvinylpyrrolidone polymer.

19. The method of claim 5, wherein the (i) fenretinide, fenretinide analog or salt thereof; and (ii) physiologically acceptable source of assimilable zinc, are formulated in the same composition.

20. The method of claim 5, wherein the CFTR modulator comprises ivacaftor (IVA, VX-770), GLPG2451, GLPG1837, lumacaftor (LUM, VX-809), tezacaftor (VX-661), VX-440, VX-152, GLPG2222, or any combination thereof.

21. The method of claim 20, wherein the CFTR modulator comprises a combination of (i) ivacaftor and lumacaftor or (ii) tezacaftor and ivacaftor.

22. The method of claim 21, wherein the combination further comprises VX-440 or VX-152.

* * * * *